(12) United States Patent
Alibakhsh

(10) Patent No.: US 12,388,721 B2
(45) Date of Patent: *Aug. 12, 2025

(54) SYSTEM AND METHOD FOR ESTABLISHING CHANNELIZED COMMUNICATIONS AND RESOURCE MANAGEMENT

(71) Applicant: Xeba Technologies, LLC, Sandy Springs, GA (US)

(72) Inventor: Massoud Alibakhsh, Sandy Springs, GA (US)

(73) Assignee: Xeba Technologies, LLC, Sandy Springs, GA (US)

( * ) Notice: Subject to any disclaimer, the term of this patent is extended or adjusted under 35 U.S.C. 154(b) by 314 days.

This patent is subject to a terminal disclaimer.

(21) Appl. No.: 18/154,426

(22) Filed: Jan. 13, 2023

(65) Prior Publication Data

US 2024/0031312 A1    Jan. 25, 2024

Related U.S. Application Data

(60) Provisional application No. 63/390,546, filed on Jul. 19, 2022.

(51) Int. Cl.
*H04L 41/22* (2022.01)
*G06F 40/40* (2020.01)
(Continued)

(52) U.S. Cl.
CPC .............. *H04L 41/22* (2013.01); *G06F 40/40* (2020.01); *G16H 50/20* (2018.01); *G16H 80/00* (2018.01);
(Continued)

(58) Field of Classification Search
CPC ...... G06Q 10/10; G06Q 10/06; G06Q 10/103; G06Q 10/0633; G06Q 10/00;
(Continued)

(56) References Cited

U.S. PATENT DOCUMENTS 8,671,097 B2    3/2014   Wu et al.
10,229,205 B1*  3/2019   Grant ................... G06F 16/951
(Continued)

FOREIGN PATENT DOCUMENTS

AU    2018100482 A4    6/2018
WO    2024020457 A2    1/2024

OTHER PUBLICATIONS

U.S. Non-Final Office Action dated Aug. 30, 2023 cited in U.S. Appl. No. 18/154,534, 13 pgs.
(Continued)

*Primary Examiner* — Soe Hlaing
*Assistant Examiner* — Abderrahmen Chouat
(74) *Attorney, Agent, or Firm* — BEKIARES ELIEZER LLP

(57) ABSTRACT

A system for establishing channelized communications and resource management for an organization. The system includes: a processor of a channel server node connected to an organization network; a memory on which are stored machine-readable instructions that when executed by the processor, cause the processor to: monitor the at least one organization network to collect analytics data, process the analytics data to identify nodes and associated pivot objects of the at least one organization network, workflow-related communication records of the at least one organization network to retrieve workflow communication data, and generate at least one communication channel configured to connect the nodes and the associated pivot objects based on the workflow communication data.

20 Claims, 6 Drawing Sheets

(51) Int. Cl.
  *G16H 50/20* (2018.01)
  *G16H 80/00* (2018.01)
  *H04L 41/0813* (2022.01)
  *H04L 41/14* (2022.01)
  *H04L 41/16* (2022.01)
  *H04L 51/04* (2022.01)
  *H04L 51/216* (2022.01)

(52) U.S. Cl.
  CPC .......... *H04L 41/0813* (2013.01); *H04L 41/14* (2013.01); *H04L 41/16* (2013.01); *H04L 51/04* (2013.01); *H04L 51/216* (2022.05)

(58) Field of Classification Search
  CPC ...... G06Q 10/101; G06Q 30/02; G06Q 30/01; G06Q 10/04; G06Q 10/06311; G06Q 10/08; G06Q 10/06316; G06Q 30/0201; G06Q 10/087; G06Q 10/06313; G06Q 50/01; G06Q 10/063118; G06Q 10/107; G06Q 30/06; G06Q 10/063114; G06Q 10/0637; G06Q 2220/10; G06Q 10/0631; G06Q 10/06393; G06Q 20/1235; G06Q 2220/00; G06Q 30/0277; G06Q 40/08; G06Q 10/0833; G06Q 10/20; G06Q 30/0202; G06Q 30/0206; G06Q 30/0641; G06Q 10/06312; G06Q 10/06315; G06Q 2220/18; G06Q 40/00; G06Q 40/02; G06Q 50/04; G06Q 10/0635; G06Q 30/00; G06Q 30/0276; G06Q 10/063112; G06Q 10/067; G06Q 10/0838; G06Q 30/0275; G06Q 30/0643; G06Q 50/02; G06Q 10/06375; G06Q 10/083; G06Q 20/10; G06Q 20/40; G06Q 30/018; G06Q 30/0239; G06Q 30/0251; G06Q 30/0601; G06Q 30/0631; G06Q 10/063; G06Q 10/0639; G06Q 10/06395; G06Q 10/1053; G06Q 20/322; G06Q 20/382; G06Q 30/0241; G06Q 30/0269; G06Q 30/0613; G06Q 50/26; G06Q 10/0835; G06Q 20/3827; G06Q 20/3829; G06Q 20/389; G06Q 20/401; G06Q 20/405; G06Q 30/0623; G06Q 50/22; G06Q 10/0834; G06Q 10/109; G06Q 10/1095; G06Q 20/02; G06Q 20/202; G06Q 20/204; G06Q 20/3223; G06Q 20/3227; G06Q 20/326; G06Q 20/3278; G06Q 20/36; G06Q 20/363; G06Q 20/367; G06Q 20/3674; G06Q 20/3825; G06Q 20/4014; G06Q 20/4015; G06Q 30/016; G06Q 30/0205; G06Q 30/0253; G06Q 30/0283; G06Q 10/02; G06Q 10/0831; G06Q 10/08345; G06Q 10/08355; G06Q 10/0875; G06Q 10/30; G06Q 20/108; G06Q 20/14; G06Q 20/145; G06Q 20/384; G06Q 20/386; G06Q 20/42; G06Q 30/015; G06Q 30/0203; G06Q 30/0204; G06Q 30/0237; G06Q 30/0243; G06Q 30/0247; G06Q 30/0249; G06Q 30/0255; G06Q 30/0256; G06Q 30/0267; G06Q 30/0271; G06Q 30/0282; G06Q 30/0607; G06Q 30/0609; G06Q 30/0611; G06Q 30/0633; G06Q 30/0637; G06Q 30/0639; G06Q 40/06; G06Q 40/12; G06Q 50/16; G06Q 50/184; G06Q 50/40; G06Q 20/027; G06Q 20/04; G06Q 20/12; G06Q 20/28; G06Q 20/321; G06Q 20/3224; G06Q 20/3255; G06Q 20/3274; G06Q 20/3276; G06Q 20/3821; G06Q 20/4016; G06Q 30/012; G06Q 30/0211; G06Q 30/0244; G06Q 30/0252; G06Q 30/0254; G06Q 30/0261; G06Q 30/0274; G06Q 30/0281; G06Q 30/0625; G06Q 30/0627; G06Q 30/0635; G06Q 50/06; G06Q 50/08; G06Q 50/10; G06Q 50/14; G06Q 50/18; G06Q 50/188; G06Q 50/265; G06Q 50/50; G06Q 50/60; H04L 67/02; H04L 9/50; H04L 51/52; H04L 63/08; H04L 51/56; H04L 51/04; H04L 63/0428; H04L 67/10; H04L 67/306; H04L 12/1822; H04L 51/18; H04L 67/51; H04L 63/20; H04L 51/046; H04L 65/4015; H04L 69/14; H04L 9/3247; H04L 9/40; H04L 51/066; H04L 65/403; H04L 51/216; H04L 63/083; H04L 67/55; H04L 69/329; H04L 67/12; H04L 9/3239; H04L 51/10; H04L 61/5007; H04L 51/214; H04L 63/18; H04L 67/535; H04L 51/08; H04L 63/0823; H04L 67/1095; H04L 67/1097; H04L 63/061; H04L 63/102; H04L 63/104; H04L 12/1827; H04L 41/22; H04L 51/02; H04L 67/06; H04L 9/3263; H04L 2209/603; H04L 2463/101; H04L 2463/102; H04L 51/42; H04L 51/48; H04L 63/0281; H04L 63/10; H04L 67/01; H04L 67/1044; H04L 67/1061; H04L 67/56; H04L 69/03; H04L 69/32; H04L 9/0822; H04L 9/0825; H04L 9/0861; H04L 9/3271; H04L 63/105; H04L 63/12; H04L 65/4038; H04L 12/1818; H04L 41/00; H04L 41/16; H04L 51/063; H04L 51/23; H04L 65/1083; H04L 67/565; H04L 69/08; H04L 9/0643; H04L 9/0891; H04L 2209/56; H04L 41/0813; H04L 41/14; H04L 51/224; H04L 63/0807; H04L 67/104; H04L 67/131; H04L 67/52; H04L 67/564; H04L 67/59; H04L 67/75; H04L 69/18; H04L 69/24; H04L 9/12; H04L 12/185; H04L 2209/42; H04L 41/046; H04L 41/40; H04L 51/212; H04L 67/025; H04L 67/34; H04L 67/62; H04L 9/007; H04L 9/3073; H04L 2101/65; H04L 41/044; H04L 41/0806; H04L 41/0893; H04L 41/0894; H04L 41/0895; H04L 41/12; H04L 41/145; H04L 45/74; H04L 47/125; H04L 51/58; H04L 61/106; H04L 61/2592; H04L 61/4511; H04L 63/0236; H04L 63/0263; H04L 63/0272; H04L 63/0815; H04L 63/101; H04L 63/126; H04L 65/1045; H04L 65/612; H04L 65/65; H04L 65/70; H04L 67/125; H04L 67/53; H04L 69/22; H04L 9/0637; H04L 9/321; H04L 9/3297; H04L 1/0041; H04L 12/1859; H04L 41/5003; H04L 43/045; H04L 43/0847; H04L 47/808; H04L 51/00; H04L 63/123; H04L 63/1483; H04L 63/166; H04L 65/1069; H04L 67/567; H04L 9/0869; H04L 9/3226; H04L 9/3242; H04L 12/18; H04L 12/4633; H04L 41/06; H04L 41/0631; H04L 41/069; H04L 41/0803; H04L 41/20; H04L 41/5041; H04L 43/00; H04L 43/0811; H04L 43/0817; H04L 43/0823; H04L 43/0852; H04L 43/0864; H04L 43/087; H04L 47/10; H04L 63/0227; H04L 63/0442; H04L 63/0492; H04L 63/0884; H04L 63/1408; H04L 63/1416; H04L 63/1425; H04L 63/1433; H04L 63/1441; H04L 65/1101; H04L 65/762; H04L 65/765; H04L 67/1074; H04L 67/14; H04L 67/141; H04L 67/60; H04L 9/0838; H04L 9/0852; H04L 9/0863; H04L 9/0894; H04L 1/0002; H04L 1/0009; H04L 1/0057; H04L 1/0076; H04L 1/16; H04L 1/18; H04L 1/1854; H04L 1/1867; H04L 1/1874; H04L 12/1813; H04L 12/1881; H04L 2101/37; H04L 2209/76; H04L 2209/805; H04L 2209/84; H04L 27/0014; H04L 41/026; H04L 41/5009; H04L 41/5074; H04L 43/08; H04L 43/14; H04L 43/50; H04L 47/783; H04L 47/828; H04L 5/0008; H04L 5/0064; H04L 51/21; H04L 61/4594; H04L 63/0407; H04L 63/0846; H04L 63/0853; H04L 63/0892; H04L 63/107; H04L 63/1466; H04L 65/00; H04L 65/103; H04L 65/104; H04L 65/1106; H04L 65/75; H04L 65/752; H04L 65/80; H04L 67/00; H04L 67/04; H04L 67/1001; H04L 67/146; H04L 67/562; H04L 67/563; H04L 67/5651; H04L 67/566; H04L 67/568; H04L 67/63; H04L 69/04; H04L 69/163; H04L 69/164; H04L 9/0656; H04L 9/088; H04L 9/0897; H04L 9/14; H04L 9/3213; H04L 9/3234; H04L 9/3236

See application file for complete search history.

(56) References Cited

U.S. PATENT DOCUMENTS

| | | | | |
|---|---|---|---|---|
| 10,938,755 | B1 * | 3/2021 | MacMillin | G06F 9/542 |
| 11,082,486 | B1 * | 8/2021 | Brevoort | H04L 65/1083 |
| 11,563,710 | B1 * | 1/2023 | MacDonald | G06F 21/31 |
| 11,694,774 | B1 * | 7/2023 | Nasrallah | G06N 20/00 |
| | | | | 705/3 |
| 11,901,080 | B1 | 2/2024 | Matt et al. | |
| 12,323,306 | B2 | 6/2025 | Alibakhsh | |
| 2004/0230466 | A1 * | 11/2004 | Davis | G06Q 10/06315 |
| | | | | 705/7.17 |
| 2013/0246525 | A1 * | 9/2013 | Patil | H04L 12/1827 |
| | | | | 709/204 |
| 2015/0106420 | A1 | 4/2015 | Warfield et al. | |
| 2015/0245084 | A1 | 8/2015 | Downing et al. | |
| 2015/0302338 | A1 * | 10/2015 | Zaveri | H04L 67/1001 |
| | | | | 705/7.39 |
| 2016/0004565 | A1 * | 1/2016 | Harper | G06Q 10/06316 |
| | | | | 718/102 |
| 2018/0176318 | A1 | 6/2018 | Rathod | |
| 2018/0284758 | A1 | 10/2018 | Cella et al. | |
| 2019/0041836 | A1 | 2/2019 | Cella et al. | |
| 2019/0064791 | A1 | 2/2019 | Cella et al. | |
| 2019/0265971 | A1 | 8/2019 | Behzadi et al. | |
| 2020/0127951 | A1 * | 4/2020 | Shah | H04L 12/1813 |
| 2020/0279658 | A1 | 9/2020 | Rao et al. | |
| 2021/0034595 | A1 * | 2/2021 | Tselikis | G06F 9/451 |
| 2021/0144169 | A1 | 5/2021 | Lasser | |
| 2021/0151140 | A1 | 5/2021 | Bates et al. | |
| 2021/0174921 | A1 | 6/2021 | Albrecht et al. | |
| 2021/0248514 | A1 | 8/2021 | Cella et al. | |
| 2022/0078797 | A1 * | 3/2022 | Helms | G06F 3/02 |
| 2022/0197306 | A1 | 6/2022 | Cella et al. | |
| 2022/0230759 | A1 | 7/2022 | Abu El Ata et al. | |
| 2022/0291666 | A1 | 9/2022 | Cella et al. | |
| 2022/0374884 | A1 | 11/2022 | Wai et al. | |
| 2023/0064752 | A1 * | 3/2023 | Kirchhof | H04L 51/046 |
| 2023/0222581 | A1 | 7/2023 | Halperin et al. | |
| 2024/0029883 | A1 | 1/2024 | Alibakhsh | |
| 2024/0031242 | A1 | 1/2024 | Alibakhsh | |
| 2024/0031245 | A1 | 1/2024 | Alibakhsh | |

OTHER PUBLICATIONS

International Search Report and Written Opinion dated Jan. 12, 2024 cited in Application No. PCT/US23/70516, 12 pgs.
International Preliminary Report on Patentability dated Jan. 30, 2025 cited in Application No. PCT/US23/70516, 9 pgs.
U.S. Non-Final Office Action dated Mar. 5, 2025 cited in U.S. Appl. No. 18/154,780, 26 pgs.
U.S. Non-Final Office Action dated Dec. 30, 2024 cited in U.S. Appl. No. 18/154,737, 17 pgs.
Related U.S. Appl. No. 19/226,266, filed Jun. 3, 2025, Applicant: Xeba Technologies, LLC, entittled "AI-Based System and Method for Establishing Channelized Communications" (copy available in IFW).

* cited by examiner

SYSTEM AND METHOD FOR ESTABLISHING CHANNELIZED COMMUNICATIONS AND RESOURCE MANAGEMENT

RELATED APPLICATIONS

Under provisions of 35 U.S.C. § 119(e), the Applicant claims benefit of U.S. Provisional Application No. 63/390,546 filed on Jul. 19, 2022, and having inventors in common, which is incorporated herein by reference in its entirety.

This patent application is related to U.S. application Ser. No. 18/154,534 filed on Jan. 13, 2023, which claims the benefit under 35 U.S.C. § 119(e) of U.S. Provisional Application No. 63/390,546 filed on Jul. 19, 2022, entitled "AI-Based System and Method for Establishing Channelized Communications", and having inventors in common, which are incorporated herein by reference in its entirety.

This patent application is related to U.S. application Ser. No. 18/154,737 filed on Jan. 13, 2023, which claims the benefit under 35 U.S.C. § 119(e) of U.S. Provisional Application No. 63/390,546 filed on Jul. 19, 2022, entitled "System and Methods for Establishing and Rendering Channelized Communication Model", and having inventors in common, which are incorporated herein by reference in its entirety.

This patent application is related to U.S. application Ser. No. 18/154,780 filed on Jan. 13, 2023, which claims the benefit under 35 U.S.C. § 119(e) of U.S. Provisional Application No. 63/390,546 filed on Jul. 19, 2022, entitled "AI-Based System and Method for Prediction of Medical Diagnosis", and having inventors in common, which are incorporated herein by reference in its entirety.

It is intended that the referenced application may be applicable to the concepts and embodiments disclosed herein, even if such concepts and embodiments are disclosed in the referenced application with different limitations and configurations and described using different examples and terminology.

FIELD OF DISCLOSURE

The present disclosure generally relates to intercorporate communications, and more particularly, to an intelligent automated system for establishing channelized communications withing an organization

BACKGROUND

There have been two waves of modern Corporate Communications. The first wave was the adoption of email and its wildly successful proliferation. However, in larger organizations with more than a dozen members, email has failed due to an inherent flaw in its model. Every user's inbox within the organization is public in a sense that any other user can send them an email, relevant or not. There have been numerous user interface tools built into various email programs, e.g., conversation modes, filters, and hardware devices designed to stop unwanted emails. These measures have all been unsuccessful, as nearly 85% of all email is now considered spam.

In dissecting human communication, there exists two components: the individual and the subject matter. An analysis of the communication model for email points to the individual as the pivot in this model. This means that email relies entirely on the individual sender to properly identify who to send emails to. In a team environment, the individual has to first assess the content of the message, and based on some real or virtual individual/function mapping table, route that message to the correct individuals in the team. While it challenging for small teams, efficient routing becomes virtually impossible as the size of the organization grows. This failure is due to the inherent shortcoming or flaw in the email model—i.e., dependency on the individuals to properly and promptly route the messages to the appropriate recipients. Using the email model, as we scale the size of the organization, the exponential rise of noise to information ratio will eventually paralyze the network and render it useless or ineffective.

The second wave of Corporate Communications was an adoption based on social media tools such as Facebook. Similar group communication systems have emerged for the corporate market such as Slack, Yammer or MS Teams. In these new models, the new pivot has now shifted to the subject matter from the individual. A manager creates communication channels with specific subject lines in advance, and individuals can then decide whether to subscribe to these channels based on their relevance to their functions or needs within the organization. This allows the receivers to choose which types of messages or communications they wish to receive. This constitutes a tremendous improvement over the email model since the recipient is given some level of control over the types of messages received. This model is superior to the email model and is somewhat effective when not only the size of the organization is small, but the team's workflow is extremely simple. The challenge here is the process of finding a proper model for communication channel creation. However, creation of the communication channel turns out to be an impossible task in modern organizations for the following reasons. Since modern teams are organized along a production line or workflow, the relevant discussions of the team members have to be focused and synchronized generally with the workflow and specifically with the objects that move around within the workflow. Representing multi-dimensional complex workflows using a series of somewhat arbitrarily named chat channels is an impossible demand on this model. The problem is exacerbated when individuals can create channels at will, and pretty soon the organization can end up with overlapping channels and/or an overwhelming number of channels. In other words, even if the subject is the new pivot, the individual still plays a significant role in creating the communication channels. Accordingly, the chat-based model fails to associate the workflow with human communications in an effective manner.

Accordingly, an intelligent automated system and method for establishing effective channelized communications withing an organization are desired.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

One embodiment of the present disclosure provides a system for establishing channelized communications and resource management for an organization. The system includes: a processor of a channel server node connected to an organization network; a memory on which are stored machine-readable instructions that when executed by the processor, cause the processor to: monitor the at least one organization network to collect analytics data, process the analytics data to identify nodes and associated pivot objects of the at least one organization network, query workflow-related communication records of the at least one organization network to retrieve workflow communication data, and generate at least one communication channel configured to connect the nodes and the associated pivot objects based on the workflow communication data.

Another embodiment of the present disclosure provides a method that includes one or more of: monitoring at least one organization network to collect analytics data, processing the analytics data to identify nodes and associated pivot objects of the at least one organization network, querying workflow-related communication records of the at least one organization network to retrieve workflow communication data, and generating at least one communication channel configured to connect the nodes and the associated pivot objects based on the workflow communication data.

Another embodiment of the present disclosure provides a computer-readable medium including instructions for monitoring at least one organization network to collect analytics data, processing the analytics data to identify nodes and associated pivot objects of the at least one organization network, querying workflow-related communication records of the at least one organization network to retrieve workflow communication data, and generating at least one communication channel configured to connect the nodes and the associated pivot objects based on the workflow communication data.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1A:
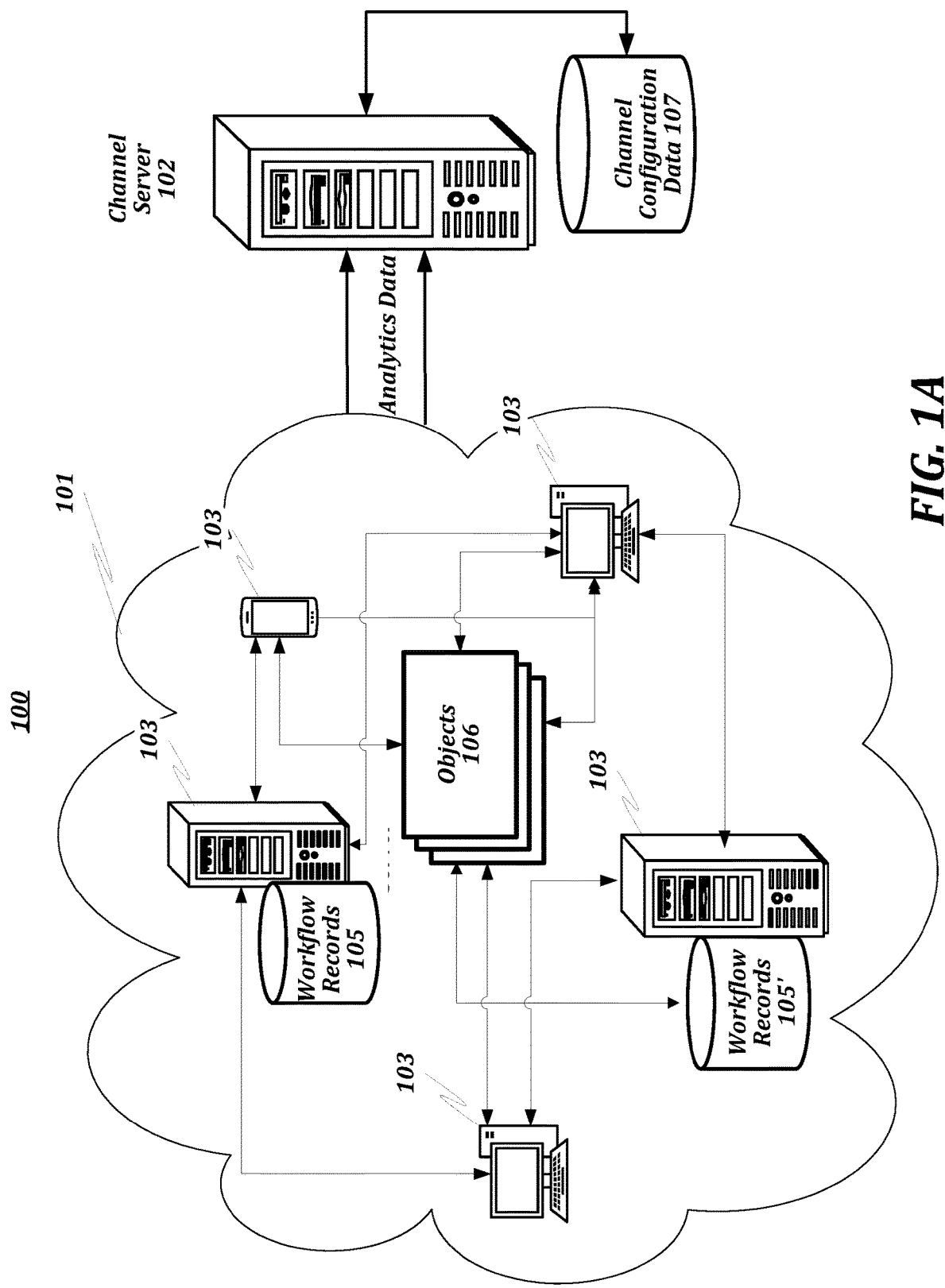
FIG. 1A illustrates a network diagram of a system for intelligent automated monitoring of communications withing an organization consistent with the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of processing job applicants, embodiments of the present disclosure are not limited to use only in this context.

The present disclosure provides a system, method and computer-readable medium for establishing effective channelized communications withing an organization.

In any modern organization, workflow-based communication is at the heart of all relevant communications within the organization. The disclosed embodiments represent a novel wave of Corporate Communications based on a communication model where communication channels are not created by individuals, but rather generated (i.e., established) based on the entities (i.e., objects) that move through the organization's workflow. This communication model automatically integrates human communication directly with the organization's workflow in an optimal manner. Note that the individual and the subject matter are not used as the pivots in the proposed model. Instead, the new pivots can be automatically identified based on analysis of the workflow itself. These pivots may be the critical entities (i.e., objects) that are, for example, moving around the production line or within the workflow. In other words, any entity or component of an entity within the workflow which may be considered critical and/or worthy of a discussion amongst the team members may be used as the new pivot of the communication model. The pivot entity has assigned attributes associated with a particular communication channel. Once the channelized communication is established (i.e., auto-generated on-the-fly), individuals within the organization may simply search a database for objects or entities of interest and may subscribe or follow that object/entity. The individuals may also use the chat channel associated with that object/entity to communicate with other individuals or interested parties (i.e., stakeholders).

For example, if the goal of a team within the organization is to make chairs, each part and/or component of the chair may be considered a pivot. Just as these components have length, color and other attributes, they may also have an associated communication channel the users (i.e., stakeholders) can communicate over with regards to the particular part/or component of the chair being moved through the production workflow. As discussed above, the stakeholders may find this communication channel by searching for this object (i.e., a part or component) in the database and connect to this object and to other stakeholders subscribed or otherwise connected to this object. The whole chair can also have a unique chat channel attribute. As a matter of fact, every single chair or its components may have their own unique communication channels or subchannels which can be the pivot for a variety of users (stakeholders) in the assembly line team.

The disclosed embodiments represent a completely different paradigm of inter-organizational communications that automatically guarantees optimal communication within organizations. This means that there are no longer any irrelevant messages. The messages are not routed by individual or arbitrary channels, but by the entities/objects of interest which are moving through the production process or workflow. Another important aspect of the disclosed communication model is that the entity/object itself can use its channel to communicate to users (stakeholders) about changes in the state of the object caused by other stakeholder entities or automatic systems. This provides the added benefit of timely communication about the state of the object to all stakeholders and allows them to react to those changes in real-time. This approach also, advantageously, centralizes and normalizes all communication about the object or entity of interest.

The disclosed communication model may not only be applicable to pure communications systems, but may be applicable to all current business software applications. Every business application such as an accounting system or an Electronic Health Records is essentially a custom communication system. These systems are based on complex state machines that manage and communicate data in a structured fashion. The structured data that is input into these systems by humans are extracted from ad-hoc human communications flowing in from a variety of sources such as phone calls, faxes, mail, discussion forums, etc. After the extraction of the structured data and inputting it into the business applications, the source is either filed away or lost completely. The new communication paradigm provides a road map to integrate all such ad-hoc communications with the structured data in one place.

As an example, within an Electronic Health Record system, a physician is examining an X-ray of her patient. She decides to ask for a consultation from a radiology specialist. She may simply open up the X-ray's chat channel and may mention or flag the radiology specialists while posing the question. The specialist receives a message from this X-ray object's chat channel, proceeds to examine the X-ray and enters his comments into the same channel. All of these back-and-forth communications are now recorded in the channel that is an attribute of the X-ray object. Since the X-ray is associated with a specific patient in the database, all other attributes of that patient are known in the system ad may be used as pivots for private communication channels.

While projects need to be completed on time, within budget, and according to specification, software development teams routinely fail to meet these requirements. Many teams assign a project manager to ensure that the project is successfully completed per the requirements. However, in existing systems it is difficult to determine whether the project manager is effectively performing their role—as so many factors can lead to the successful completion of a project and existing systems lack the transparency necessary to make an accurate determination of whether individual resources were competent with their specific tasks. Some organization use project management applications that lack proper communication channels. In one embodiment, automated generation of the chat channels is provided based on monitoring of the organization's communications, current workflow and infrastructure.

FIG. 1A illustrates a network diagram of a system for intelligent automated monitoring of communications withing an organization consistent with the present disclosure.

Referring to FIG. 1A, the example network 100 includes a channel server node 102 connected to an organization network 101 including a variety of organization user (i.e., stakeholder) nodes 103 and objects 106. As discussed above, the objects 106 are the entities of interest to the stakeholders of the nodes 103. As a non-limiting example, the object may reflect an element of a production product associated with the production workflow, a medical file (e.g., X-ray, MRI, etc.) that is of interest to the organization's (e.g., a hospital) doctors and technicians participating in a medical evaluation/diagnosis workflow or a contract or another legal document that is being accessed and modified or commented on by attorneys and paralegals of the law firm as part of legal process workflow. The organization network 101 may also include workflow-related communication records databases 105 for recording the communications of the organization. As can be seen from FIG. 1A, the nodes 103 may communicate with each other in nearly random fashion, where some of the nodes 103 may get communications related to the object(s) 106 that is not of any interest to the stakeholder associated with the particular node 103.

Figure 1B:
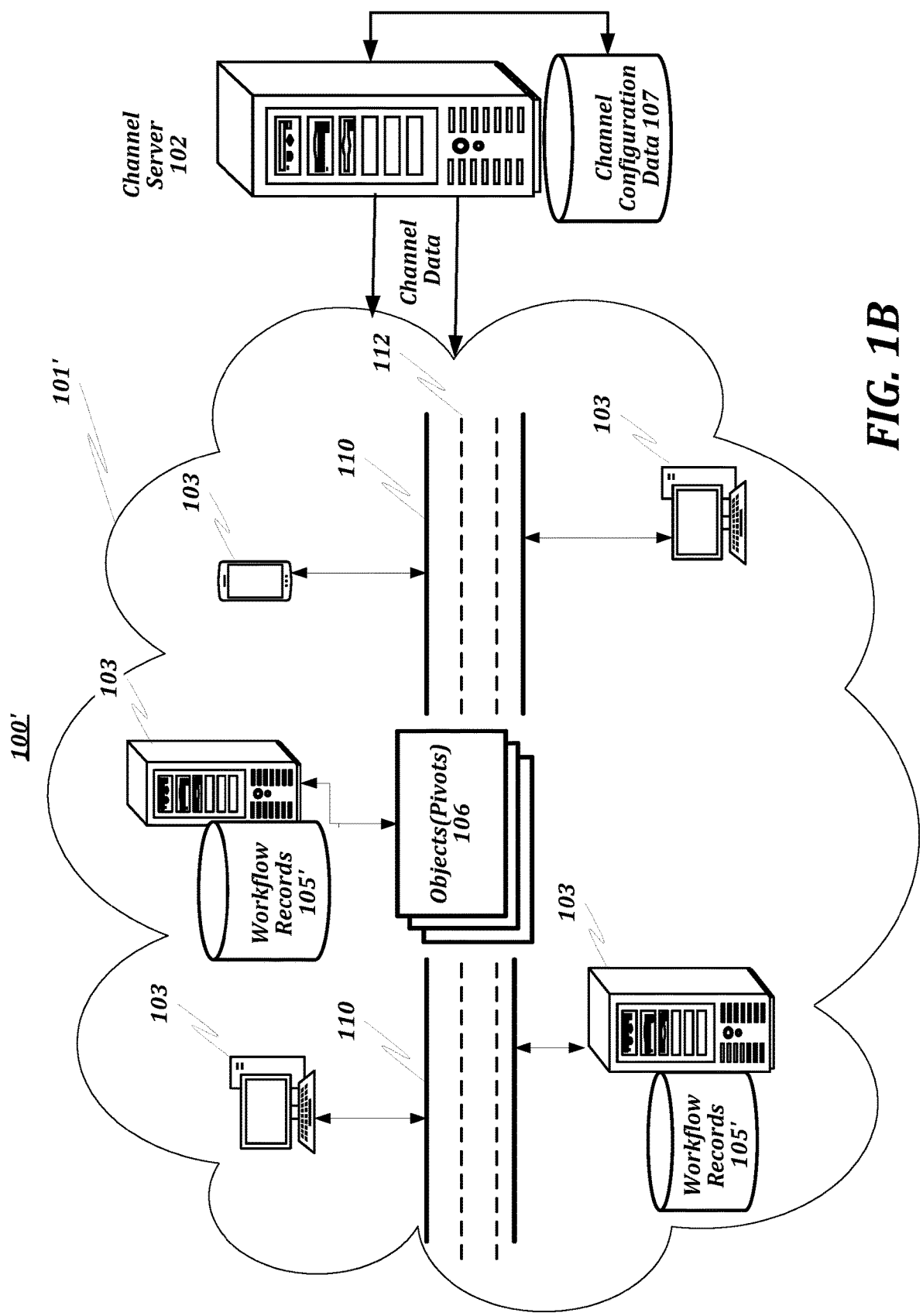
FIG. 1B illustrates a network diagram of an intelligent automated system for establishing effective channelized communications withing an organization, consistent with the present disclosure.

The channel server node 102 may monitor the organization network 101 to determine the workflow data and the pivot objects 106. The channel server 102 may access the workflow-related communication records databases 105 to acquire additional workflow communication data reflecting communications between the nodes 103. Then, the channel server 102 may analyze the collected analytics data to generate the organization communication channels (and sub-channels) based on the pivot objects 106 and the workflow data of the organization network 101 as shown in FIG. 1B. The channel server 102 may use channel configuration data accumulated through previous analysis of the organization network 101.

FIG. 1B illustrates a network diagram of an intelligent automated system for establishing effective channelized communications withing an organization, consistent with the present disclosure.

Referring to FIG. 1B, the example network 100' includes a channel server node 102 connected to an organization network 101' including a variety of organization user (i.e., stakeholder) nodes 103 and objects 106. As discussed above, the objects 106 are the entities of interest to the stakeholders of the nodes 103. The organization network 101' represents the channelized model of the organization network 101 (see FIG. 1A) generated by the channel server node 102 based on the analytics data acquired through monitoring of the organization network 101 (FIG. 1A). As can be seen from FIG. 1B, the organization network 101' is now configured to have communication channels 110 and subchannels 112 generated based on the pivots—i.e., pivot objects 106 that have properties defining what nodes 103 should be communicating with each other over the communication channels 110 and subchannels 112. Using the pervious X-ray example, a doctor at one of the nodes 103 may be associated with the X-ray object 106 over a patient's X-ray communication channel. The doctor may be interested in an opinion of another doctor or a radiologist. In this case, the doctor may add a request (i.e., a new property) to the X-ray object 106 indicating another doctor or the radiologist. Now, this doctor or radiologist at another node 103 is automatically added to this patient's X-ray communication channel. This way, the channelized model provides for the most efficient communications where only the interested parties (i.e., stakeholders) communicate with each other with regards to the object of interest while all other communications that are not relevant to them are implemented over other channels 110 or subchannels and 112.

As discussed above, the channel server node 102 uses the analytics data including workflow-related communication records data 105 acquired through monitoring of the organization network 101 (see FIG. 1A). The channel configuration data may be recorded in the database 107 residing on or connected to the channel server node 102 that may be a cloud server or an edge server. The channel configuration data may be used for generation or modification of the communication channels 110 based on new pivot objects 106 being introduced into the organization or modification of the objects 106. In one embodiment, the channels 110 may be reconfigured or additional subchannels 112 may be added based on new nodes 103 being added to the organization network 101'. For example, a new doctor joins the group, a new diagnostic equipment is added, a new product workflow is introduced, etc.

As discussed above, the disclosed embodiments depicted in FIG. 1B provide a communications layer that forms the fabric of an informative expression (i.e., a communication of information/data) in the channel configuration database 107. The communications layer consists of nodes corresponding to the pivot objects in the channel configuration database 107. The pivot objects correspond to any element of the database for which a dialog/communication is determined to exist or have the potential to exist. The nodes 103, in turn, are associated with the communication channels 110/112 in this new communications layer which is integrated into the existing channel configuration database 107 (or formed along with the database).

Each node 103 is tied to the pivot object(s) 106. The nodes 103 can be grouped together, or related to each other, based on the underlying relationship of the pivot objects 106 they are associated with (i.e., based on parent, siblings, children relationship). Such grouping may be reflected in the UI as "tiers of nodes." The nodes 103, in turn, may serve as relays of information between the nodes themselves and to the end-users (i.e., interested stakeholders) of the underlying pivot objects 106 associated therewith. As the underlying pivot object 106 undergoes the workflow process, the stakeholders at the nodes 103 are kept apprised and are able to follow the pivot object 106 through its workflow process, as it goes from Tier to Tier, and as it becomes associated/unassociated with other nodes 103 or groups of entities.

According to the disclosed embodiments, the integration of the communications layer into the channel configuration database 107 includes forming nodes of expression (both informative expression and actionable expression) that are based on identified pivot points associated with the pivot objects 106 within the channel configuration database 107. Note that the pivot objects 106 are the critical objects representing any objects in the database that require discussion by organization members (i.e., stakeholders) or present data for communication to the organization members.

As discussed above, the nodes 103 are associated with pivot objects 106 in the channel configuration database 107. A node of an informative expression is a forum for the input or output of:

Output of Textual and Graphical Representations related to the database;

Input of Parameters or Operational commands.

The node may allow multiple types of expression:

i. Expression from a user about the node and/or the critical object associated with the node; and ii. Expression from the object regarding any changes made thereto.

Expression may be implemented in human-readable terms, such as natural language. Expression may be attributed to a user who caused the change of the pivot object. In one embodiment, expression may be received from another node or pivot object that affects this pivot object:

i.e., informative expressions generated by the node and presented to the user, relating to a status/activity of the underlying pivot object or pivot objects related thereto (or derivative expression associated therewith); and pivot points serving as points of data relay between the targeted objects in the database.

The disclosed embodiments enable the conversation to follow the entity/object, as the entity/object travels through the workflow, and the user(s) to engage in a dialog related to the entity/object in one place with all relevant information. In one embodiment, any entity (pivot object) that organization members can discuss with verbal communication, has an additional attribute that contains dialog about the pivot object associated with the dialog. The pivot points provide access to:

1. Data and parameters associated with the entities/pivot objects;
2. Surrounding data/relevant data to the entities/pivot objects.

The pivot point may ensure that all contextually relevant information is presented at the node, so that the user would not need to navigate through the underlying database system to obtain relevant information. The nodes may enable publishing of informative expression associated with the related pivot object(s). The channelized communication system may generate the informative expression to be presented within the node based on an activity within the node (e.g., changes to a property of the pivot object associated with the node); and an activity related to the node (e.g., changes to a property of a different pivot object that affects this pivot object).

The channelized communication system may communicate the state of the pivot object by the expression that may be attributed to a user who caused a change in the critical object, but still be presented by the node itself. In one embodiment, the nodes may be structured into tiers based on one or more of:

i. The underlying structure of the pivot objects;

ii. One or more workflows associated with the pivot objects.

In one embodiment, the nodes may form a network of multi-directional channeling of the informative expression (i.e., data). In this way, the nodes form relays of informative expression. In turn, the network of nodes forms the fabric of the channelized communication layer that provides a new-age of communication of informative expressions relating to pivot objects in the channel configuration database. Note that the stakeholders of each node 103 may self-identify and/or may be selected based on user activity monitored by the channel server 102. The channel server 102 may identify pivot objects 106 and the associated stakeholders, and automatically add the stakeholders to the corresponding nodes 103. The channelized communication system provided by the channel server 102 may provide access to the informative expressions of each node 103 to its stakeholders. channelized communication system may enable the stakeholders to add expressions into the Input Port of the node 103. The expression may be propagated through the relays in the node network as needed. Rules engine may be used to determine when to propagate the expression and/or to which connected nodes 103 the expression should be propagated. Alert indications or notifications may be provided to the stakeholders when the node 103 or an associated pivot object 106 are updated (e.g., when one or more informative expressions are published).

According to the disclosed embodiments, conducting communication of informative expression within the channelized communication system is implemented as follows. In one embodiment, each node 103 may track its activity (e.g., activity of a pivot object 106 associated with the node 103). Each node 103 may "talk" to related nodes to receive updates on their activity. Relations may be transitory—i.e., relations may have set beginning and/or ending times, and relations may form/break when the corresponding stakeholders follow and 'unfollow' the organization network. Furthermore, relations may be identified by a user and may be identified by the channelized communication system. Each node 103 may be configured to alert stakeholders in a derivative data point (e.g., a related node) of associated activity of the node and related activity of the related node.

In one embodiment, a channel configuration database may be used for project management. The channelized communication system may be integrated with the channel configuration database based on an expression layer that may include multiple forums for publishing the expression. Each forum may be associated with a corresponding pivot object via an attribute of the object. The channel server 102 may analyze workflow-related communication records databases 105 to identify and extract pivot objects—e.g., objects that move through a workflow. As discussed above, pivot object may serve as pivot points into the expression layer that is being constructed for the organization on top of the existing organization's network. Workflows within the Project Management System may be replicated by the channelized communication system because the communication pivot points are tied to the pivot objects. Organization of the communication pivot points may mirror the organization of the pivot objects within the workflow stored in the workflow-related communication records databases 105.

Figure 2:
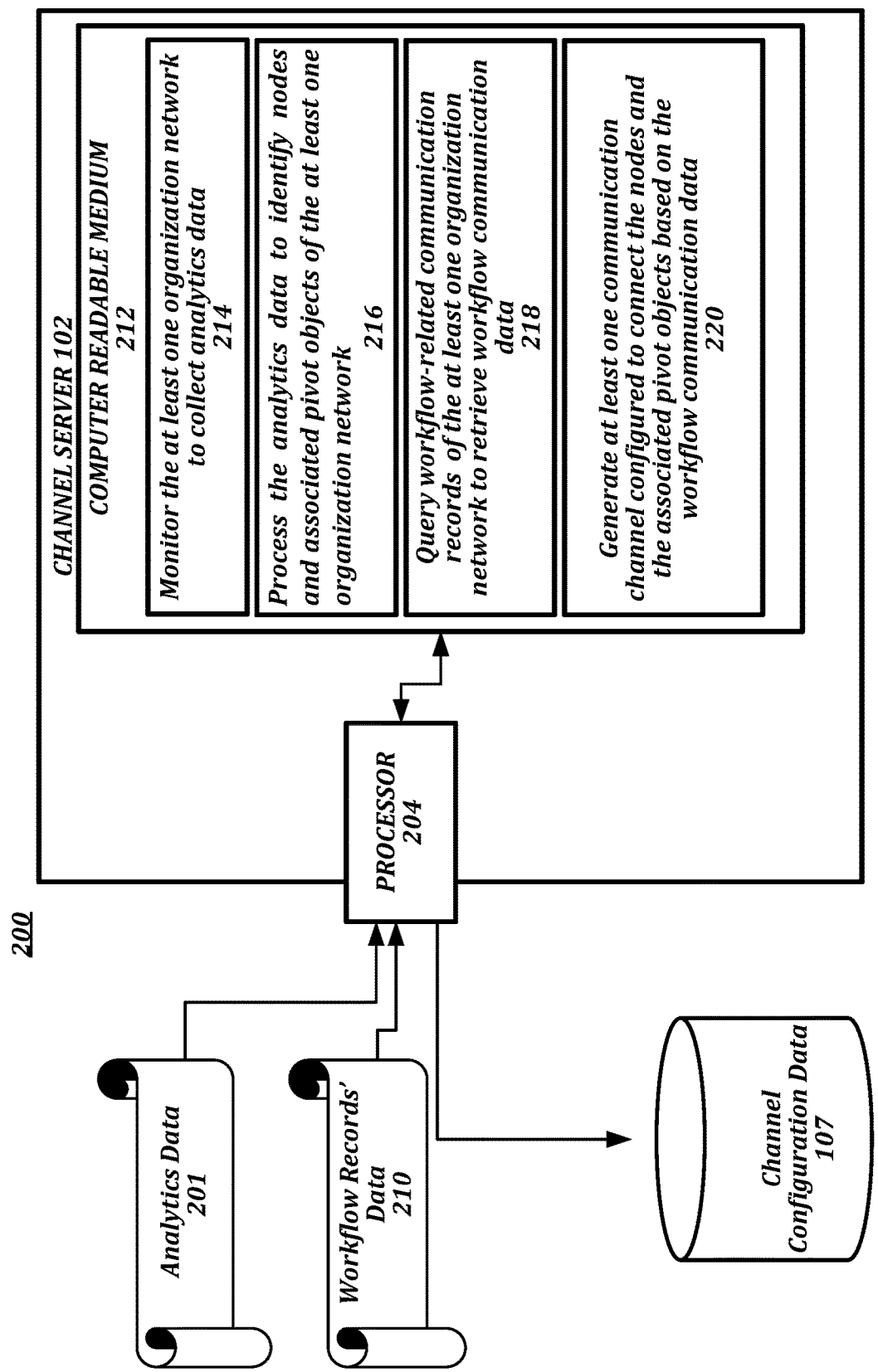
FIG. 2 illustrates a network diagram of a system including detailed features of a channel server node consistent with the present disclosure.

FIG. 2 illustrates a network diagram of a system including detailed features of a channel server node 102 consistent with the present disclosure.

Referring to FIG. 2, the example network 200 includes the channel server node 102 connected to a channel configuration database 107. As discussed above with respect to FIG. 1A, the channel server node 102 may monitor the organization network and infrastructure to acquire real-time analytics data 201 that may include pivot objects, organization user nodes, communications data, etc. The channel server node 102 may also acquire workflow-related communication records data 210 from the workflow-related communication records databases 105 (see FIG. 1A).

While this example describes in detail only one channel server node 102, multiple such nodes may be connected to the network. It should be understood that the channel server node 102 may include additional components and that some of the components described herein may be removed and/or modified without departing from a scope of the channel server node 102 disclosed herein. The channel server node 102 may be a computing device or a server computer, or the like, and may include a processor 204, which may be a semiconductor-based microprocessor, a central processing unit (CPU), an application specific integrated circuit (ASIC), a field-programmable gate array (FPGA), and/or another hardware device. Although a single processor 204 is depicted, it should be understood that the channel server node 102 may include multiple processors, multiple cores, or the like, without departing from the scope of the channel server node 102 system.

The channel server node 102 may also include a non-transitory computer readable medium 212 that may have stored thereon machine-readable instructions executable by the processor 204. Examples of the machine-readable instructions are shown as 214-220 and are further discussed below. Examples of the non-transitory computer readable medium 212 may include an electronic, magnetic, optical, or other physical storage device that contains or stores executable instructions. For example, the non-transitory computer readable medium 212 may be a Random-Access memory (RAM), an Electrically Erasable Programmable Read-Only Memory (EEPROM), a hard disk, an optical disc, or other type of storage device.

The processor 204 may fetch, decode, and execute the machine-readable instructions 214 to monitor at least one organization network to collect analytics data 201. The processor 204 may fetch, decode, and execute the machine-readable instructions 216 to process the analytics data to identify nodes and associated pivot objects of the at least one organization network. The processor 204 may fetch, decode, and execute the machine-readable instructions 218 to query workflow-related communication records of the at least one organization network to retrieve workflow communication data. The processor 204 may fetch, decode, and execute the machine-readable instructions 220 to generate at least one communication channel configured to connect the nodes and the associated pivot objects based on the workflow communication data.

Figure 3A:
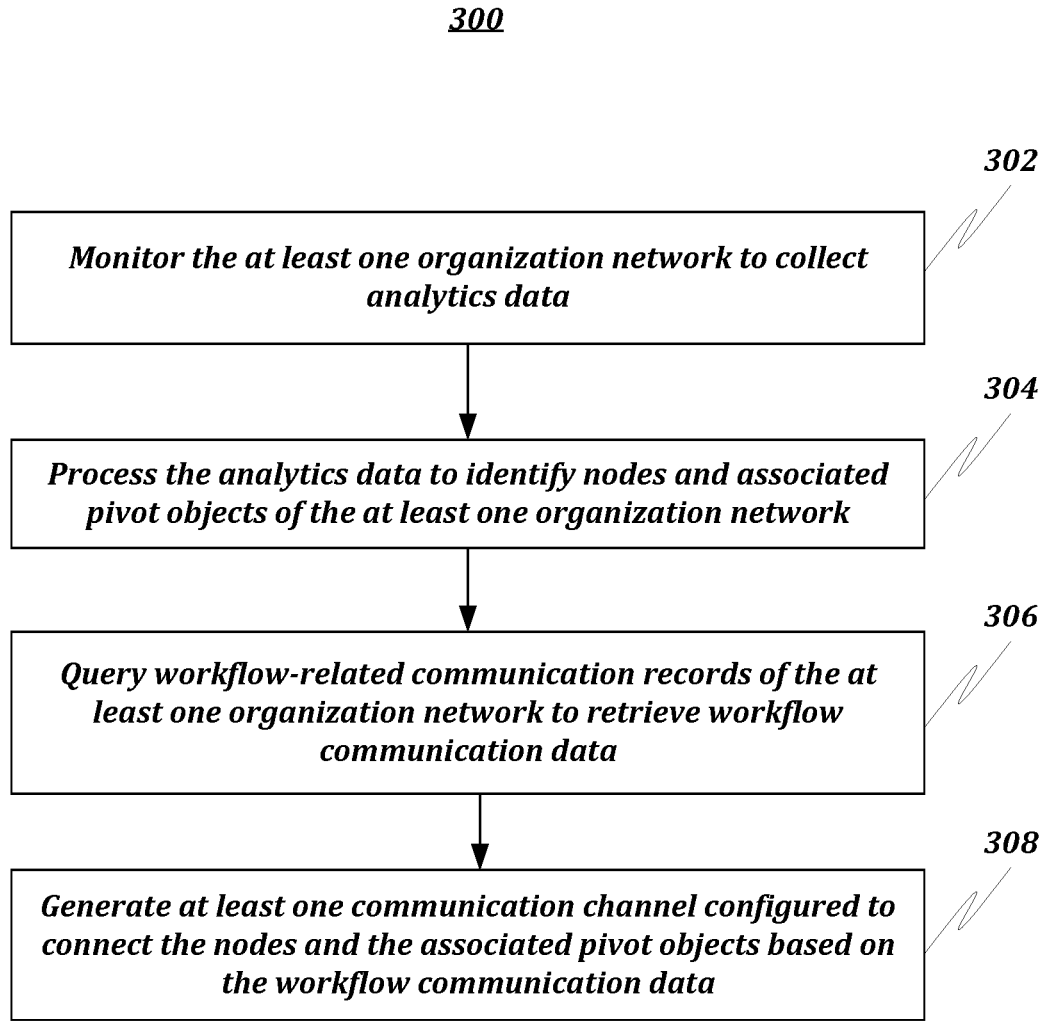
FIG. 3A illustrates a flowchart of a method for establishing effective channelized communications within an organization consistent with the present disclosure.

FIG. 3A illustrates a flowchart of a method for establishing effective channelized communications within an organization consistent with the present disclosure.

Referring to FIG. 3A, the method 300 may include one or more of the steps described below. FIG. 3A illustrates a flow chart of an example method executed by the channel server 102 (see FIG. 2). It should be understood that method 300 depicted in FIG. 3A may include additional operations and that some of the operations described therein may be removed and/or modified without departing from the scope of the method 300. The description of the method 300 is also made with reference to the features depicted in FIG. 2 for purposes of illustration. Particularly, the processor 204 of the channel server 102 may execute some or all of the operations included in the method 300.

With reference to FIG. 3A, at block 302, the processor 204 may monitor the at least one organization network to collect analytics data. At block 304, the processor 204 may process the analytics data to identify nodes and associated pivot objects of the at least one organization network. At block 306, the processor 204 may query com workflow-related communication records of the at least one organization network to retrieve workflow communication data. At block 308, the processor 204 may generate at least one communication channel configured to connect the nodes and the associated pivot objects based on the workflow communication data.

Figure 3B:
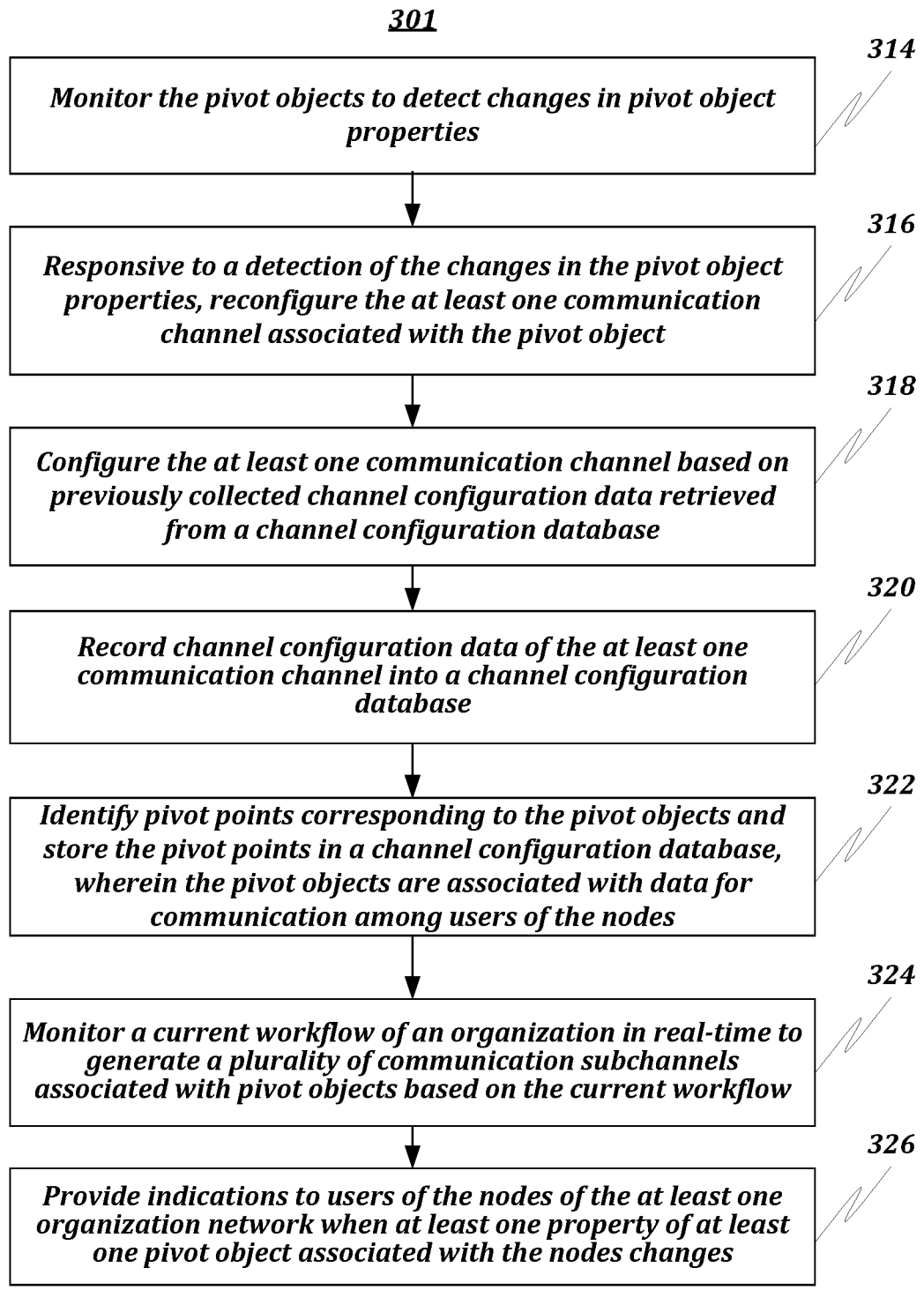
FIG. 3B illustrates a further flow chart of a method establishing effective channelized communications withing an organization consistent with the present disclosure.

FIG. 3B illustrates a further flowchart of a method for establishing effective channelized communications within an organization consistent with the present disclosure. Referring to FIG. 3B, the method 301 may include one or more of the steps described below. FIG. 3B illustrates a flow chart of an example method executed by the channel server 102 (see FIG. 2). It should be understood that method 301 depicted in FIG. 3B may include additional operations and that some of the operations described therein may be removed and/or modified without departing from the scope of the method 301. The description of the method 301 is also made with reference to the features depicted in FIG. 2 for purposes of illustration. Particularly, the processor 204 of the channel server 102 may execute some or all of the operations included in the method 301.

With reference to FIG. 3B, at block 314, the processor 204 may monitor the pivot objects to detect changes in pivot object properties. At block 316, the processor 204 may, responsive to a detection of the changes in the pivot object properties, reconfigure the at least one communication channel associated with the pivot object. At block 318, the processor 204 may configure the at least one communication channel based on previously collected channel configuration data retrieved from a channel configuration database. At block 320, the processor 204 may record channel configuration data of the at least one communication channel into a channel configuration database. At block 322, the processor 204 may identify pivot points corresponding to the pivot objects and store the pivot points in a channel configuration database, wherein the pivot objects are associated with data for communication among users of the nodes. At block 324, the processor 204 may monitor a current workflow of an organization in real-time to generate a plurality of communication subchannels associated with pivot objects based on the current workflow. At block 326, the processor 204 may provide indications to users of the nodes of the at least one organization network when at least one property of at least one pivot object associated with the nodes changes. Note that the reconfiguring of the communication channel may result in addition of nodes associated with the pivot object and/or elimination of nodes no longer associated with the pivot object.

The proposed claims provide a new and improved system architecture that is designed to improve the functioning of computing systems at transmitting key data and information between critical objects of a multi-dimensional object-based records system. Existing architecture provides an outdated methodology for facilitating the communication of data within computing systems. Embodiments contemplate the Provision of a UI capable of providing the same.

Consistent with embodiments of the present disclosure, a communications layer may be adapted into a new or pre-existing objective-oriented data model/work-flow capable database [collectively referred to as 'Database']. Non-limiting examples of a compatible database (as used herein) would be, for example, a record management system with clients, accounts, patients, projects, matters, and other file types, which may further include CRMs and production related work-flow capable systems. Each of the aforementioned database parameters may be referred to as data elements.

Still consistent with embodiments of the present disclosure, the communications layer may enable the composition, recordation, transmission, and receipt of messages related to various elements of the database to which the communications layer is adapted. In this instance, the communications layer may be represented as the layer through which an informative expression (i.e., a communication of information/data) is communicated in the database.

In various embodiments, the communications layer may be comprised of nodes, which corresponds to the critical objects in the database. The critical objects correspond to any element of the database for which a dialog/communication is determined to exist or have the potential to exist. The stage of determining which database elements may be construed as, or generated as, critical objects are discussed throughout the present disclosure.

Still consistent with various embodiments of the present disclosure, the nodes, in turn, may effectively serve the 'channels' of communication in this new communications layer which is integrated into the existing database (or formed along with the database). In this way, each node may be tied to the critical objects. It should be understood that the terms critical object and 'entities' may refer to one another.

Still consistent with various embodiments the present disclosure, the nodes may be grouped together, or related to each other, based on the underlying relationship of the critical objects they are associated with (e.g., parent, siblings, cousins, children). With reference to a User-Interface presentation, in some embodiments, such grouping may be reflected in the UI as 'tiers' of nodes.

The nodes may be configured to serve as 'relays' of information (informative expressions) between the nodes themselves and to end-users who are interested stakeholders of the underlying objects associated therewith (e.g., data elements in the database, determined to be a critical object in the communications layer). As the underlying object undergoes a workflow process associated with the database, the communication layer may be configured to keep the stakeholders apprised. In this way, the stakeholders may be enabled to follow the object through its workflow process, as it goes from Tier to Tier, and as it becomes associated/unassociated with other entities or groups of entities.

Accordingly, in various embodiments, aspects of the present disclosure may provide at least the following.
a. The integration of the communications layer into the Database forming nodes of expression (both informative expression and actionable expression) that are based on identified pivot points within the database.
   i. The identified pivot points corresponding to [critical] objects in the database
   ii. The critical objects can be any objects in the database that require discussion by humans, or present data for communication to humans (see b(ii))
b. The nodes being tied to/integrated with critical objects in the database.
   i. A node of informative expression is a forum for the input & output of:
      1. Output of Textual & Graphical Representations related to the Database.
      2. Input of Parameters or Operational commands.
   ii. The node can allow multiple types of expression:
      1. Expression from a human about the node and/or the critical object associated with the node
      2. Expression from the object regarding any changes made thereto
         a. Expression may be in human-readable terms, such as natural language
         b. Expression may be attributed to a human who caused the change
      3. Expression from another node or critical object that affects this critical object:
         a. i.e., informative expressions generated by the node and presented to the human, relating to a status/activity of the underlying object or objects related thereto (or derivative expression associated therewith)
c. The pivot points serving as points of data relay between the targeted objects in the database. This enables the conversation to follow the entity, as the entity travels through the workflow, and the user to engage in dialog in one place with all relevant information.
   i. Any entity (critical object) that humans can discuss with verbal communication, should have an additional attribute that contains dialog about the critical object associated with the dialog.
   ii. The Pivot Points provide access to:
      1. Data and parameters associated with the entities/critical objects
      2. Surrounding data/relevant data to the entities/critical objects
      3. Pivot points connect key participants
   iii. Ensures all contextually relevant information is presented at the node, so that the user would not need to navigate through the underlying database system to obtain relevant information.
d. The nodes enabling the publishing of informative expression associated with the related critical object(s)
   i. Wherein the system generates the informative expression to be presented within the node based on:
      1. Activity within the node (e.g., changes to a property of the critical object associated with the node); and
      2. Activity related to the node (e.g., changes to a property of a different critical object that affects this critical object)
   ii. Communicates the state of the object
   iii. The expression may be attributed to a human who caused a change in the critical object, but still be presented by the node itself.
e. The nodes being structured into tiers based on one or more of:
   i. The underlying structure of the critical objects
   ii. One or more workflows associated with the critical objects
   iii. Also the chatter going on between parties
f. The nodes forming a network of multi-directional channeling of the informative expression (i.e., data)
   i. In this way, the nodes form relays of informative expression
   ii. In turn, the network of nodes forms the fabric of the communication layer that provides a new-age of communication of informative expressions relating to critical objects in the Database
g. Additional Stages (outside of independent):
   i. The identification of stakeholders for each node
      1. Stakeholders may self-identify and/or may be selected based on user activity
      2. The system can identify critical objects and the associated stakeholders, and automatically add the stakeholders to the corresponding nodes
   ii. Providing access to the informative expressions of each node to its stakeholders.
   iii. Enabling the stakeholders to add expressions into the Input Port of the Node.
      1. The expression being propagated through the relays in the node network) as needed a. Rules engine may be used to determine:
   i. when to propagate the expression; and/or
   ii. to which connected nodes the expression should be propagated
 iv. Providing alerts to the stakeholders when the node is updated (e.g., when one or more informative expressions are published).

Embodiments of the present disclosure may provide systems and methods for information to be communicated within the database and up to the stakeholders, between the stakeholders, and back down from the stakeholders into the database. The following aspects relate to, at least in part, communications layer's process of conducting the transfer of information between the nodes and the users.

Accordingly, in various embodiments, aspects of the present disclosure may provide at least the following.
 a. Each node tracks its activity (e.g., activity of a critical object associated with the node)
 b. Each node talks to related nodes to receive updates on their activity
   v. Relations can be transitory
     1. Relations may have set beginning and/or ending times
     2. Relations may form/break, and the corresponding stakeholders can follow and 'unfollow' this network.
   vi. Relations may be identified by a user
   vii. Relations may be identified by the system
 c. Each node alerts stakeholders in a derivative data point (e.g., a related node) of associated activity of the node and related activity of the related node.

Embodiments of the present disclosure may provide methods and systems for integrating the communications layer of the present disclosure into existing database systems. Non-limiting examples of a compatible systems (as used herein) would be, for example, a record management system with clients, accounts, patients, projects, matters, and other file types, which may further include CRMs and production related work-flow capable systems. Each of the aforementioned database parameters may be referred to as data elements.

Accordingly, in various embodiments, aspects of the present disclosure may provide at least the following.
 a. Integration into [Database]
   i. Purpose of this Database is Project Management
   ii. Integration is performed with the goal of providing a communication layer into the Database
     1. Expression layer includes multiple forums for publishing the expression
     2. each forum is associated with (e.g., an attribute of) a corresponding critical object
 b. Identifying critical objects
   iii. Platform studies the database to identify and extract critical objects—e.g., an object that moves through a workflow tracked by the [Database]
   iv. Critical objects, in turn, serve as pivot points into the expression layer that is being constructed on TOP of the [Database]
   v. Establishing communication pivot points associated with the identified critical objects
     3. By creating the forums associated with each of the critical objects
 c. Giving each of the critical objects a forum of informative expression
   vi. The communications layer limited to these pivot points, and the users cannot generate an expression forum without first generating a critical object in the [Database]
   vii. The objects speak for themselves and study the system to relay what is happening
     4. Objects provide status update when one or more object properties change
     5. Objects may attribute their speech to a user who caused the change in the object
 d. Organizing the communication pivot points into classes [or 'tiers" if more appropriate term] of communication
   viii. Identifying Workflows within the Project Management System
   ix. Because the communication pivot points are tied to the critical objects, the organization of the communication pivot points may mirror the organization of the critical objects in the [Database]
 e. Tracking activity related to the critical objects
   x. The activity being associated with:
     6. The critical objects
     7. Any objects related to the critical objects
       a. Relations may be permanent or transitory
     8. A related class of critical objects
       a. Parent
       b. Sibling
       c. Child
 f. Expressing, through the forum of informative expression tied to the critical object, a derivative expression associated with the tracked activity Accordingly, in various embodiments, aspects of the present disclosure may provide at least the following.

Embodiments of the present disclosure may provide methods and systems for optimizing production-related communication of information related to critical entities in the production.

Here, embodiments of the present disclosure may provide for the establishing a forum (or channel) of communication based on entity and various objects therein, as a matter of workflow-based entities rather than free-form channel creation. In this way, channels now spawn off the entity/objects therein, rather than free-form end-user creation of channels as provided in conventional systems.

In some embodiments, critical objects may be tied to a workflow from their conception rather than be conceived then later tied to a workflow. In further embodiments, work-flows may be generated first within a project management solution or other computing platform. In turn, the communications lawyer may establish nodes that spawn based on the critical entities/objects identified to be within those workflows. In this way, those certain parameters of the workflow (e.g., entities/objects) serve as the pivot points for the communication forums.

Still consistent with various embodiments, a stake holder of a critical object can be informed on the workflow's overall [state of operation/status updates/relevant communication] from the perspective of the critical object they follow. Thus, a stakeholder may be enabled to view the entire workflow from the relevant perspective of the critical object they follow.

Aspects of the embodiments disclosed herein present disclosure eliminate the conventional need to:
create channels of communication
organize channels of communication
track channels of communication
integrate channels of communication with Project Management Workflow update the channels of communication with updates in corresponding Project Management Workflows receive messages that a stakeholder does not need Aspects of the embodiments herein provide such technical advantages by, for example, but not limited to:
1. Connecting to a Project Management System/EHR/Accounting Systems
2. Identifying Entities/Objects in the System
3. Identifying Stakeholders
4. Tracking their Workflows within the System
5. Spawning Forums of Communication based on the Pivot Points (Entities within workflows)
6. Updating (via, for example, notifications) the Forums based on the Entities progress
7. Integrating AI into the process Embodiments of the present disclosure may provide a user interface (UI). Conventional systems provide a Dashboard UI of Channels for a user to participate in. In contrast, and according to various embodiments, a user rather need to only select critical objects to follow, and the corresponding channel notifications will be provided dynamically to the user in a user interface. This, in turn, eliminates the need for a user to choose and follow channels. Rather, all the relevant messages applicable to objects that the user follows is provided to a user in an inbox-like interface. Since the messages are provided to the user, the user no longer needs to access an object record and search for a communication thread related thereto.

Accordingly, in various embodiments, aspects of the present disclosure may provide at least the following.
  a) Enabling users to join/follow forums based on their stake/interest in an object or entity.
    a. Instead of users joining channels, users not follow objects/entities—and then, are notified of the updates related thereto.
    b. the channels of communication that they interface with are automatically provided to them based on the progress of the object/entity that they follow.
  b) Provide an interface for managing these communications generated by the system in following the entities through the workflows.
  c) Connecting to a Project Management software to identify 'entities'. These 'entities' serve as 'channels.' Channel creation is disclosed throughout the present disclosure.
  d) Tiered Organization—The interface is organized by tiers (nugget, sprint, project, build, etc.).

Accordingly, in various embodiments, aspects of the present disclosure may provide at least the following.
  a. A user may be enable d to identify a node to join, or auto-assigned to a node.
    viii. Search for Objects within the Database
    ix. Subscribe to the Nodes of the Communication Layer associated with those Objects
    x. As the subscribed objects tie into other classes (tiers) then, in turn, the user may get subscriptions to those nodes as well.
      1. May receive all communications from the related objects, or only those which affect the object to which the user is subscribed
      2. Use of rules engine to determine when user receives notifications form related objects
    xi. As the object ties are broken, then, in turn, user loses their subscription to those nodes.
    xii. Adding users to a channel based on their relationship to the critical entity.

In this way, if the original entity a user is following gets associated with another entity, embodiments may enable the user to auto-follow that other entity, when it's relevant (using, for example, AI- and machine learning).

The above embodiments of the present disclosure may be implemented in hardware, in a computer-readable instructions executed by a processor, in firmware, or in a combination of the above. The computer computer-readable instructions may be embodied on a computer-readable medium, such as a storage medium. For example, the computer computer-readable instructions may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative embodiment, the processor and the storage medium may reside as discrete components. For example, FIG. 4 illustrates an example computing device (e.g., a server node) 400, which may represent or be integrated in any of the above-described components, etc.

Figure 4:
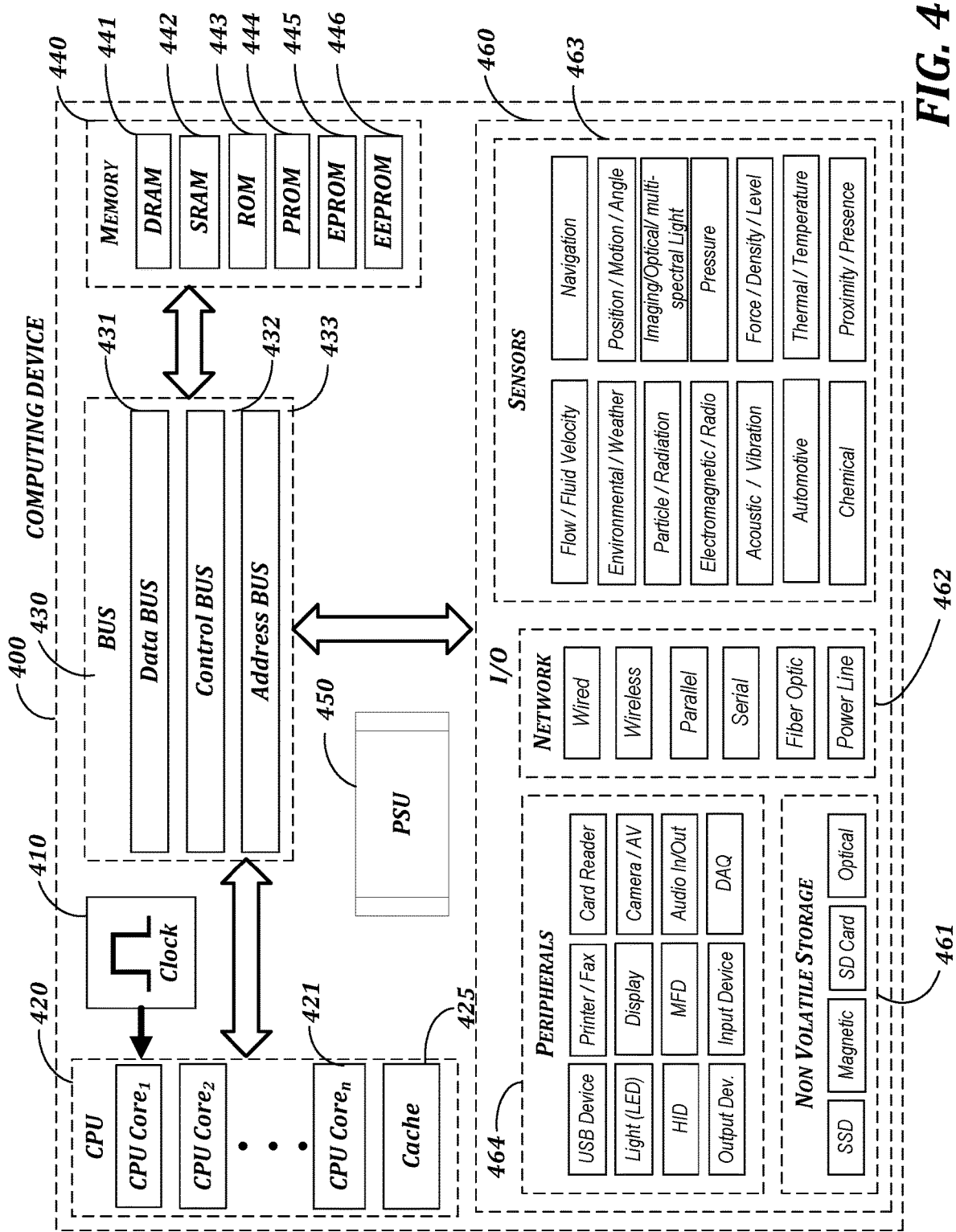
FIG. 4 illustrates a block diagram of a system including a computing device for performing the method of FIGS. 3A and 3B.

FIG. 4 illustrates a block diagram of a system including computing device 400. The computing device 400 may comprise, but not be limited to the following:

Mobile computing device, such as, but is not limited to, a laptop, a tablet, a smartphone, a drone, a wearable, an embedded device, a handheld device, an Arduino, an industrial device, or a remotely operable recording device;

A supercomputer, an exa-scale supercomputer, a mainframe, or a quantum computer;

A minicomputer, wherein the minicomputer computing device comprises, but is not limited to, an IBM AS500/iSeries/System I, A DEC VAX/PDP, a HP3000, a Honeywell-Bull DPS, a Texas Instruments TI-990, or a Wang Laboratories VS Series;

A microcomputer, wherein the microcomputer computing device comprises, but is not limited to, a server, wherein a server may be rack mounted, a workstation, an industrial device, a raspberry pi, a desktop, or an embedded device;

The channel server node 102 (see FIG. 2) may be hosted on a centralized server or on a cloud computing service. Although method 300 has been described to be performed by the channel server node 102 implemented on a computing device 400, it should be understood that, in some embodiments, different operations may be performed by a plurality of the computing devices 400 in operative communication at least one network.

Embodiments of the present disclosure may comprise a computing device having a central processing unit (CPU) 420, a bus 430, a memory unit 440, a power supply unit (PSU) 450, and one or more Input/Output (I/O) units. The CPU 420 coupled to the memory unit 440 and the plurality of I/O units 460 via the bus 430, all of which are powered by the PSU 450. It should be understood that, in some embodiments, each disclosed unit may actually be a plurality of such units for the purposes of redundancy, high availability, and/or performance. The combination of the presently disclosed units is configured to perform the stages any method disclosed herein.

Consistent with an embodiment of the disclosure, the aforementioned CPU 420, the bus 430, the memory unit 450, a PSU 450, and the plurality of I/O units 460 may be implemented in a computing device, such as computing device 400. Any suitable combination of hardware, software, or firmware may be used to implement the aforementioned units. For example, the CPU 420, the bus 430, and the memory unit 450 may be implemented with computing device 400 or any of other computing devices 400, in combination with computing device 400. The aforementioned system, device, and components are examples and other systems, devices, and components may comprise the aforementioned CPU 420, the bus 430, the memory unit 450, consistent with embodiments of the disclosure.

At least one computing device 400 may be embodied as any of the computing elements illustrated in all of the attached figures, including the channel node 102 (FIG. 2). A computing device 400 does not need to be electronic, nor even have a CPU 420, nor bus 430, nor memory unit 440. The definition of the computing device 400 to a person having ordinary skill in the art is "A device that computes, especially a programmable [usually] electronic machine that performs high-speed mathematical or logical operations or that assembles, stores, correlates, or otherwise processes information." Any device which processes information qualifies as a computing device 400, especially if the processing is purposeful.

With reference to FIG. 4, a system consistent with an embodiment of the disclosure may include a computing device, such as computing device 400. In a basic configuration, computing device 400 may include at least one clock module 410, at least one CPU 420, at least one bus 430, and at least one memory unit 440, at least one PSU 450, and at least one I/O 460 module, wherein I/O module may be comprised of, but not limited to a non-volatile storage sub-module 461, a communication sub-module 462, a sensors sub-module 463, and a peripherals sub-module 465.

A system consistent with an embodiment of the disclosure the computing device 400 may include the clock module 410 may be known to a person having ordinary skill in the art as a clock generator, which produces clock signals. Clock signal is a particular type of signal that oscillates between a high and a low state and is used like a metronome to coordinate actions of digital circuits. Most integrated circuits (ICs) of sufficient complexity use a clock signal in order to synchronize different parts of the circuit, cycling at a rate slower than the worst-case internal propagation delays. The preeminent example of the aforementioned integrated circuit is the CPU 420, the central component of modern computers, which relies on a clock. The only exceptions are asynchronous circuits such as asynchronous CPUs. The clock 410 can comprise a plurality of embodiments, such as, but not limited to, single-phase clock which transmits all clock signals on effectively 1 wire, two-phase clock which distributes clock signals on two wires, each with non-overlapping pulses, and four-phase clock which distributes clock signals on 5 wires.

Many computing devices 400 use a "clock multiplier" which multiplies a lower frequency external clock to the appropriate clock rate of the CPU 420. This allows the CPU 420 to operate at a much higher frequency than the rest of the computer, which affords performance gains in situations where the CPU 420 does not need to wait on an external factor (like memory 440 or input/output 460). Some embodiments of the clock 410 may include dynamic frequency change, where, the time between clock edges can vary widely from one edge to the next and back again.

A system consistent with an embodiment of the disclosure the computing device 400 may include the CPU unit 420 comprising at least one CPU Core 421. A plurality of CPU cores 421 may comprise identical CPU cores 421, such as, but not limited to, homogeneous multi-core systems. It is also possible for the plurality of CPU cores 421 to comprise different CPU cores 421, such as, but not limited to, heterogeneous multi-core systems, big.LITTLE systems and some AMD accelerated processing units (APU). The CPU unit 420 reads and executes program instructions which may be used across many application domains, for example, but not limited to, general purpose computing, embedded computing, network computing, digital signal processing (DSP), and graphics processing (GPU). The CPU unit 420 may run multiple instructions on separate CPU cores 421 at the same time. The CPU unit 420 may be integrated into at least one of a single integrated circuit die and multiple dies in a single chip package. The single integrated circuit die and multiple dies in a single chip package may contain a plurality of other aspects of the computing device 400, for example, but not limited to, the clock 410, the CPU 420, the bus 430, the memory 450, and I/O 460.

The CPU unit 420 may contain cache 422 such as, but not limited to, a level 1 cache, level 2 cache, level 3 cache or combination thereof. The aforementioned cache 422 may or may not be shared amongst a plurality of CPU cores 421. The cache 422 sharing comprises at least one of message passing and inter-core communication methods may be used for the at least one CPU Core 421 to communicate with the cache 422. The inter-core communication methods may comprise, but not limited to, bus, ring, two-dimensional mesh, and crossbar. The aforementioned CPU unit 420 may employ symmetric multiprocessing (SMP) design.

The plurality of the aforementioned CPU cores 421 may comprise soft microprocessor cores on a single field programmable gate array (FPGA), such as semiconductor intellectual property cores (IP Core). The plurality of CPU cores 421 architecture may be based on at least one of, but not limited to, Complex instruction set computing (CISC), Zero instruction set computing (ZISC), and Reduced instruction set computing (RISC). At least one of the performance-enhancing methods may be employed by the plurality of the CPU cores 421, for example, but not limited to Instruction-level parallelism (ILP) such as, but not limited to, super-scalar pipelining, and Thread-level parallelism (TLP).

Consistent with the embodiments of the present disclosure, the aforementioned computing device 400 may employ a communication system that transfers data between components inside the aforementioned computing device 400, and/or the plurality of computing devices 400. The aforementioned communication system will be known to a person having ordinary skill in the art as a bus 430. The bus 430 may embody internal and/or external plurality of hardware and software components, for example, but not limited to a wire, optical fiber, communication protocols, and any physical arrangement that provides the same logical function as a parallel electrical bus. The bus 430 may comprise at least one of, but not limited to a parallel bus, wherein the parallel bus carry data words in parallel on multiple wires, and a serial bus, wherein the serial bus carry data in bit-serial form. The bus 430 may embody a plurality of topologies, for example, but not limited to, a multidrop/electrical parallel topology, a daisy chain topology, and a connected by switched hubs, such as USB bus. The bus 430 may comprise a plurality of embodiments, for example, but not limited to:

Internal data bus (data bus) 431/Memory bus
Control bus 432

Address bus 433
System Management Bus (SMBus)
Front-Side-Bus (FSB)
External Bus Interface (EBI)
Local bus
Expansion bus
Lightning bus
Controller Area Network (CAN bus)
Camera Link
ExpressCard
Advanced Technology management Attachment (ATA), including embodiments and derivatives such as, but not limited to, Integrated Drive Electronics (IDE)/Enhanced IDE (EIDE), ATA Packet Interface (ATAPI), Ultra-Direct Memory Access (UDMA), Ultra ATA (UATA)/Parallel ATA (PATA)/Serial ATA (SATA), CompactFlash (CF) interface, Consumer Electronics ATA (CE-ATA)/Fiber Attached Technology Adapted (FATA), Advanced Host Controller Interface (AHCI), SATA Express (SATAe)/External SATA (eSATA), including the powered embodiment eSATAp/Mini-SATA (mSATA), and Next Generation Form Factor (NGFF)/M.2.
Small Computer System Interface (SCSI)/Serial Attached SCSI (SAS)
HyperTransport
InfiniBand
RapidIO
Mobile Industry Processor Interface (MIPI)
Coherent Processor Interface (CAPI)
Plug-n-play
1-Wire
Peripheral Component Interconnect (PCI), including embodiments such as, but not limited to, Accelerated Graphics Port (AGP), Peripheral Component Interconnect eXtended (PCI-X), Peripheral Component Interconnect Express (PCI-e) (e.g., PCI Express Mini Card, PCI Express M.2 [Mini PCIe v2], PCI Express External Cabling [ePCIe], and PCI Express OCuLink [Optical Copper{Cu} Link]), Express Card, AdvancedTCA, AMC, Universal IO, Thunderbolt/Mini DisplayPort, Mobile PCIe (M-PCIe), U.2, and Non-Volatile Memory Express (NVMe)/Non-Volatile Memory Host Controller Interface Specification (NVMHCIS).
Industry Standard Architecture (ISA), including embodiments such as, but not limited to Extended ISA (EISA), PC/XT-bus/PC/AT-bus/PC/105 bus (e.g., PC/105-Plus, PCI/105-Express, PCI/105, and PCI-105), and Low Pin Count (LPC).
Music Instrument Digital Interface (MIDI)
Universal Serial Bus (USB), including embodiments such as, but not limited to, Media Transfer Protocol (MTP)/Mobile High-Definition Link (MHL), Device Firmware Upgrade (DFU), wireless USB, InterChip USB, IEEE 1395 Interface/Firewire, Thunderbolt, and eXtensible Host Controller Interface (xHCI).

Consistent with the embodiments of the present disclosure, the aforementioned computing device 400 may employ hardware integrated circuits that store information for immediate use in the computing device 400, know to the person having ordinary skill in the art as primary storage or memory 440. The memory 440 operates at high speed, distinguishing it from the non-volatile storage sub-module 461, which may be referred to as secondary or tertiary storage, which provides slow-to-access information but offers higher capacities at lower cost. The contents contained in memory 440, may be transferred to secondary storage via techniques such as, but not limited to, virtual memory and swap. The memory 440 may be associated with addressable semiconductor memory, such as integrated circuits consisting of silicon-based transistors, used for example as primary storage but also other purposes in the computing device 400. The memory 440 may comprise a plurality of embodiments, such as, but not limited to volatile memory, non-volatile memory, and semi-volatile memory. It should be understood by a person having ordinary skill in the art that the ensuing are non-limiting examples of the aforementioned memory:

Volatile memory which requires power to maintain stored information, for example, but not limited to, Dynamic Random-Access Memory (DRAM) 551, Static Random-Access Memory (SRAM) 452, CPU Cache memory 425, Advanced Random-Access Memory (A-RAM), and other types of primary storage such as Random-Access Memory (RAM).

Non-volatile memory which can retain stored information even after power is removed, for example, but not limited to, Read-Only Memory (ROM) 453, Programmable ROM (PROM) 455, Erasable PROM (EPROM) 455, Electrically Erasable PROM (EEPROM) 456 (e.g., flash memory and Electrically Alterable PROM [EAPROM]), Mask ROM (MROM), One Time Programable (OTP) ROM/Write Once Read Many (WORM), Ferroelectric RAM (FeRAM), Parallel Random-Access Machine (PRAM), Split-Transfer Torque RAM (STT-RAM), Silicon Oxime Nitride Oxide Silicon (SONOS), Resistive RAM (RRAM), Nano RAM (NRAM), 3D XPoint, Domain-Wall Memory (DWM), and millipede memory.

Semi-volatile memory which may have some limited non-volatile duration after power is removed but loses data after said duration has passed. Semi-volatile memory provides high performance, durability, and other valuable characteristics typically associated with volatile memory, while providing some benefits of true non-volatile memory. The semi-volatile memory may comprise volatile and non-volatile memory and/or volatile memory with battery to provide power after power is removed. The semi-volatile memory may comprise, but not limited to spin-transfer torque RAM (STT-RAM).

Consistent with the embodiments of the present disclosure, the aforementioned computing device 400 may employ the communication system between an information processing system, such as the computing device 400, and the outside world, for example, but not limited to, human, environment, and another computing device 400. The aforementioned communication system will be known to a person having ordinary skill in the art as I/O 460. The I/O module 460 regulates a plurality of inputs and outputs with regard to the computing device 400, wherein the inputs are a plurality of signals and data received by the computing device 400, and the outputs are the plurality of signals and data sent from the computing device 400. The I/O module 460 interfaces a plurality of hardware, such as, but not limited to, non-volatile storage 461, communication devices 462, sensors 463, and peripherals 465. The plurality of hardware is used by the at least one of, but not limited to, human, environment, and another computing device 400 to communicate with the present computing device 400. The I/O module 460 may comprise a plurality of forms, for example, but not limited to channel I/O, port mapped I/O, asynchronous I/O, and Direct Memory Access (DMA).

Consistent with the embodiments of the present disclosure, the aforementioned computing device 400 may employ the non-volatile storage sub-module 461, which may be referred to by a person having ordinary skill in the art as one of secondary storage, external memory, tertiary storage, off-line storage, and auxiliary storage. The non-volatile storage sub-module 461 may not be accessed directly by the CPU 420 without using intermediate area in the memory 440. The non-volatile storage sub-module 461 does not lose data when power is removed and may be two orders of magnitude less costly than storage used in memory module, at the expense of speed and latency. The non-volatile storage sub-module 461 may comprise a plurality of forms, such as, but not limited to, Direct Attached Storage (DAS), Network Attached Storage (NAS), Storage Area Network (SAN), nearline storage, Massive Array of Idle Disks (MAID), Redundant Array of Independent Disks (RAID), device mirroring, off-line storage, and robotic storage. The non-volatile storage sub-module (461) may comprise a plurality of embodiments, such as, but not limited to:

Optical storage, for example, but not limited to, Compact Disk (CD) (CD-ROM/CD-R/CD-RW), Digital Versatile Disk (DVD) (DVD-ROM/DVD-R/DVD+R/DVD-RW/DVD+RW/DVD±RW/DVD+R DL/DVD-RAM/HD-DVD), Blu-ray Disk (BD) (BD-ROM/BD-R/BD-RE/BD-R DL/BD-RE DL), and Ultra-Density Optical (UDO).

Semiconductor storage, for example, but not limited to, flash memory, such as, but not limited to, USB flash drive, Memory card, Subscriber Identity Module (SIM) card, Secure Digital (SD) card, Smart Card, CompactFlash (CF) card, Solid-State Drive (SSD) and memristor.

Magnetic storage such as, but not limited to, Hard Disk Drive (HDD), tape drive, carousel memory, and Card Random-Access Memory (CRAM).

Phase-change memory

Holographic data storage such as Holographic Versatile Disk (HVD).

Molecular Memory

Deoxyribonucleic Acid (DNA) digital data storage

Consistent with the embodiments of the present disclosure, the aforementioned computing device 400 may employ the communication sub-module 462 as a subset of the I/O 460, which may be referred to by a person having ordinary skill in the art as at least one of, but not limited to, computer network, data network, and network. The network allows computing devices 400 to exchange data using connections, which may be known to a person having ordinary skill in the art as data links, between network nodes. The nodes comprise network computer devices 400 that originate, route, and terminate data. The nodes are identified by network addresses and can include a plurality of hosts consistent with the embodiments of a computing device 400. The aforementioned embodiments include, but not limited to personal computers, phones, servers, drones, and networking devices such as, but not limited to, hubs, switches, routers, modems, and firewalls.

Two nodes can be said are networked together, when one computing device 400 is able to exchange information with the other computing device 400, whether or not they have a direct connection with each other. The communication sub-module 462 supports a plurality of applications and services, such as, but not limited to World Wide Web (WWW), digital video and audio, shared use of application and storage computing devices 400, printers/scanners/fax machines, email/online chat/instant messaging, remote control, distributed computing, etc. The network may comprise a plurality of transmission mediums, such as, but not limited to conductive wire, fiber optics, and wireless. The network may comprise a plurality of communications protocols to organize network traffic, wherein application-specific communications protocols are layered, may be known to a person having ordinary skill in the art as carried as payload, over other more general communications protocols. The plurality of communications protocols may comprise, but not limited to, IEEE 802, ethernet, Wireless LAN (WLAN/Wi-Fi), Internet Protocol (IP) suite (e.g., TCP/IP, UDP, Internet Protocol version 5 [IPv5], and Internet Protocol version 6 [IPv6]), Synchronous Optical Networking (SONET)/Synchronous Digital Hierarchy (SDH), Asynchronous Transfer Mode (ATM), and cellular standards (e.g., Global System for Mobile Communications [GSM], General Packet Radio Service [GPRS], Code-Division Multiple Access [CDMA], and Integrated Digital Enhanced Network [IDEN]).

The communication sub-module 462 may comprise a plurality of size, topology, traffic control mechanism and organizational intent. The communication sub-module 462 may comprise a plurality of embodiments, such as, but not limited to:

Wired communications, such as, but not limited to, coaxial cable, phone lines, twisted pair cables (ethernet), and InfiniBand.

Wireless communications, such as, but not limited to, communications satellites, cellular systems, radio frequency/spread spectrum technologies, IEEE 802.11 Wi-Fi, Bluetooth, NFC, free-space optical communications, terrestrial microwave, and Infrared (IR) communications. Wherein cellular systems embody technologies such as, but not limited to, 3G, 5G (such as WiMax and LTE), and 5G (short and long wavelength).

Parallel communications, such as, but not limited to, LPT ports.

Serial communications, such as, but not limited to, RS-232 and USB.

Fiber Optic communications, such as, but not limited to, Single-mode optical fiber (SMF) and Multi-mode optical fiber (MMF).

Power Line and wireless communications

The aforementioned network may comprise a plurality of layouts, such as, but not limited to, bus network such as ethernet, star network such as Wi-Fi, ring network, mesh network, fully connected network, and tree network. The network can be characterized by its physical capacity or its organizational purpose. Use of the network, including user authorization and access rights, differ accordingly. The characterization may include, but not limited to nanoscale network, Personal Area Network (PAN), Local Area Network (LAN), Home Area Network (HAN), Storage Area Network (SAN), Campus Area Network (CAN), backbone network, Metropolitan Area Network (MAN), Wide Area Network (WAN), enterprise private network, Virtual Private Network (VPN), and Global Area Network (GAN).

Consistent with the embodiments of the present disclosure, the aforementioned computing device 400 may employ the sensors sub-module 463 as a subset of the I/O 460. The sensors sub-module 463 comprises at least one of the devices, modules, and subsystems whose purpose is to detect events or changes in its environment and send the information to the computing device 400. Sensors are sensitive to the measured property, are not sensitive to any property not measured, but may be encountered in its application, and do not significantly influence the measured property. The sensors sub-module 463 may comprise a plurality of digital devices and analog devices, wherein if an analog device is used, an Analog to Digital (A-to-D) converter must be employed to interface the said device with the computing device 400. The sensors may be subject to a plurality of deviations that limit sensor accuracy. The sensors sub-module 463 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors. It should be understood by a person having ordinary skill in the art that the ensuing are non-limiting examples of the aforementioned sensors:

Chemical sensors, such as, but not limited to, breathalyzer, carbon dioxide sensor, carbon monoxide/smoke detector, catalytic bead sensor, chemical field-effect transistor, chemiresistor, electrochemical gas sensor, electronic nose, electrolyte-insulator-semiconductor sensor, energy-dispersive X-ray spectroscopy, fluorescent chloride sensors, holographic sensor, hydrocarbon dew point analyzer, hydrogen sensor, hydrogen sulfide sensor, infrared point sensor, ion-selective electrode, nondispersive infrared sensor, microwave chemistry sensor, nitrogen oxide sensor, olfactometer, optode, oxygen sensor, ozone monitor, pellistor, pH glass electrode, potentiometric sensor, redox electrode, zinc oxide nanorod sensor, and biosensors (such as nano-sensors).

Automotive sensors, such as, but not limited to, air flow meter/mass airflow sensor, air-fuel ratio meter, AFR sensor, blind spot monitor, engine coolant/exhaust gas/cylinder head/transmission fluid temperature sensor, hall effect sensor, wheel/automatic transmission/turbine/vehicle speed sensor, airbag sensors, brake fluid/engine crankcase/fuel/oil/tire pressure sensor, camshaft/crankshaft/throttle position sensor, fuel/oil level sensor, knock sensor, light sensor, MAP sensor, oxygen sensor (o2), parking sensor, radar sensor, torque sensor, variable reluctance sensor, and water-in-fuel sensor.

Acoustic, sound and vibration sensors, such as, but not limited to, microphone, lace sensor (guitar pickup), seismometer, sound locator, geophone, and hydrophone.

Electric current, electric potential, magnetic, and radio sensors, such as, but not limited to, current sensor, Daly detector, electroscope, electron multiplier, faraday cup, galvanometer, hall effect sensor, hall probe, magnetic anomaly detector, magnetometer, magnetoresistance, MEMS magnetic field sensor, metal detector, planar hall sensor, radio direction finder, and voltage detector.

Environmental, weather, moisture, and humidity sensors, such as, but not limited to, actinometer, air pollution sensor, bedwetting alarm, ceilometer, dew warning, electrochemical gas sensor, fish counter, frequency domain sensor, gas detector, hook gauge evaporimeter, humistor, hygrometer, leaf sensor, lysimeter, pyranometer, pyrgeometer, psychrometer, rain gauge, rain sensor, seismometers, SNOTEL, snow gauge, soil moisture sensor, stream gauge, and tide gauge.

Flow and fluid velocity sensors, such as, but not limited to, air flow meter, anemometer, flow sensor, gas meter, mass flow sensor, and water meter.

Ionizing radiation and particle sensors, such as, but not limited to, cloud chamber, Geiger counter, Geiger-Muller tube, ionization chamber, neutron detection, proportional counter, scintillation counter, semiconductor detector, and thermoluminescent dosimeter.

Navigation sensors, such as, but not limited to, air speed indicator, altimeter, attitude indicator, depth gauge, fluxgate compass, gyroscope, inertial navigation system, inertial reference unit, magnetic compass, MHD sensor, ring laser gyroscope, turn coordinator, variometer, vibrating structure gyroscope, and yaw rate sensor.

Position, angle, displacement, distance, speed, and acceleration sensors, such as, but not limited to, accelerometer, displacement sensor, flex sensor, free fall sensor, gravimeter, impact sensor, laser rangefinder, LIDAR, odometer, photoelectric sensor, position sensor such as, but not limited to, GPS or Glonass, angular rate sensor, shock detector, ultrasonic sensor, tilt sensor, tachometer, ultra-wideband radar, variable reluctance sensor, and velocity receiver.

Imaging, optical and light sensors, such as, but not limited to, CMOS sensor, LiDAR, multi-spectral light sensor, colorimeter, contact image sensor, electro-optical sensor, infra-red sensor, kinetic inductance detector, LED as light sensor, light-addressable potentiometric sensor, Nichols radiometer, fiber-optic sensors, optical position sensor, thermopile laser sensor, photodetector, photodiode, photomultiplier tubes, phototransistor, photoelectric sensor, photoionization detector, photomultiplier, photoresistor, photoswitch, phototube, scintillometer, Shack-Hartmann, single-photon avalanche diode, superconducting nanowire single-photon detector, transition edge sensor, visible light photon counter, and wavefront sensor.

Pressure sensors, such as, but not limited to, barograph, barometer, boost gauge, bourdon gauge, hot filament ionization gauge, ionization gauge, McLeod gauge, Oscillating U-tube, permanent downhole gauge, piezometer, Pirani gauge, pressure sensor, pressure gauge, tactile sensor, and time pressure gauge.

Force, Density, and Level sensors, such as, but not limited to, bhangmeter, hydrometer, force gauge or force sensor, level sensor, load cell, magnetic level or nuclear density sensor or strain gauge, piezo-capacitive pressure sensor, piezoelectric sensor, torque sensor, and viscometer.

Thermal and temperature sensors, such as, but not limited to, bolometer, bimetallic strip, calorimeter, exhaust gas temperature gauge, flame detection/pyrometer, Gardon gauge, Golay cell, heat flux sensor, microbolometer, microwave radiometer, net radiometer, infrared/quartz/resistance thermometer, silicon bandgap temperature sensor, thermistor, and thermocouple.

Proximity and presence sensors, such as, but not limited to, alarm sensor, doppler radar, motion detector, occupancy sensor, proximity sensor, passive infrared sensor, reed switch, stud finder, triangulation sensor, touch switch, and wired glove.

Consistent with the embodiments of the present disclosure, the aforementioned computing device 400 may employ the peripherals sub-module 462 as a subset of the I/O 460. The peripheral sub-module 465 comprises ancillary devices uses to put information into and get information out of the computing device 400. There are 3 categories of devices comprising the peripheral sub-module 465, which exist based on their relationship with the computing device 400, input devices, output devices, and input/output devices.

Input devices send at least one of data and instructions to the computing device 400. Input devices can be categorized based on, but not limited to:

- Modality of input, such as, but not limited to, mechanical motion, audio, visual, and tactile.
- Whether the input is discrete, such as but not limited to, pressing a key, or continuous such as, but not limited to position of a mouse.
- The number of degrees of freedom involved, such as, but not limited to, two-dimensional mice vs three-dimensional mice used for Computer-Aided Design (CAD) applications.

Output devices provide output from the computing device 400. Output devices convert electronically generated information into a form that can be presented to humans. Input/output devices perform that perform both input and output functions. It should be understood by a person having ordinary skill in the art that the ensuing are non-limiting embodiments of the aforementioned peripheral sub-module 465:

Input Devices

- Human Interface Devices (HID), such as, but not limited to, pointing device (e.g., mouse, touchpad, joystick, touchscreen, game controller/gamepad, remote, light pen, light gun, Wii remote, jog dial, shuttle, and knob), keyboard, graphics tablet, digital pen, gesture recognition devices, magnetic ink character recognition, Sip-and-Puff (SNP) device, and Language Acquisition Device (LAD).
- High degree of freedom devices, that require up to six degrees of freedom such as, but not limited to, camera gimbals, Cave Automatic Virtual Environment (CAVE), and virtual reality systems.
- Video Input devices are used to digitize images or video from the outside world into the computing device 400. The information can be stored in a multitude of formats depending on the user's requirement. Examples of types of video input devices include, but not limited to, digital camera, digital camcorder, portable media player, webcam, Microsoft Kinect, image scanner, fingerprint scanner, barcode reader, 3D scanner, laser rangefinder, eye gaze tracker, computed tomography, magnetic resonance imaging, positron emission tomography, medical ultrasonography, TV tuner, and iris scanner.
- Audio input devices are used to capture sound. In some cases, an audio output device can be used as an input device, in order to capture produced sound. Audio input devices allow a user to send audio signals to the computing device 400 for at least one of processing, recording, and carrying out commands. Devices such as microphones allow users to speak to the computer in order to record a voice message or navigate software. Aside from recording, audio input devices are also used with speech recognition software. Examples of types of audio input devices include, but not limited to microphone, Musical Instrumental Digital Interface (MIDI) devices such as, but not limited to a keyboard, and headset.
- Data Acquisition (DAQ) devices convert at least one of analog signals and physical parameters to digital values for processing by the computing device 400. Examples of DAQ devices may include, but not limited to, Analog to Digital Converter (ADC), data logger, signal conditioning circuitry, multiplexer, and Time to Digital Converter (TDC).

Output Devices may further comprise, but not be limited to:

- Display devices, which convert electrical information into visual form, such as, but not limited to, monitor, TV, projector, and Computer Output Microfilm (COM). Display devices can use a plurality of underlying technologies, such as, but not limited to, Cathode-Ray Tube (CRT), Thin-Film Transistor (TFT), Liquid Crystal Display (LCD), Organic Light-Emitting Diode (OLED), MicroLED, E Ink Display (ePaper) and Refreshable Braille Display (Braille Terminal).
- Printers, such as, but not limited to, inkjet printers, laser printers, 3D printers, solid ink printers and plotters.
- Audio and Video (AV) devices, such as, but not limited to, speakers, headphones, amplifiers and lights, which include lamps, strobes, DJ lighting, stage lighting, architectural lighting, special effect lighting, and lasers.
- Other devices such as Digital to Analog Converter (DAC)

Input/Output Devices may further comprise, but not be limited to, touchscreens, networking device (e.g., devices disclosed in network 462 sub-module), data storage device (non-volatile storage 461), facsimile (FAX), and graphics/sound cards.

All rights including copyrights in the code included herein are vested in and the property of the Applicant. The Applicant retains and reserves all rights in the code included herein, and grants permission to reproduce the material only in connection with reproduction of the granted patent and for no other purpose.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A system, comprising:
   a processor of a channel server node connected to at least one organization network;
   a memory on which are stored machine-readable instructions that when executed by the processor, cause the processor to:
   monitor the at least one organization network to collect analytics data,
   process the analytics data to identify nodes and associated pivot objects of the at least one organization network,
   query workflow-related communication records of the at least one organization network to retrieve workflow communication data, and
   generate at least one communication channel configured to connect the nodes and the associated pivot objects based on the workflow communication data.

2. The system of claim 1, wherein the instructions further cause the processor to monitor the pivot objects to detect changes in pivot object properties.

3. The system of claim 2, wherein the instructions further cause the processor to, responsive to a detection of the changes in the pivot object properties, reconfigure the at least one communication channel associated with the pivot object.

4. The system of claim 3, wherein the reconfiguring the at least one communication channel comprises any of:
  addition of nodes associated with the pivot object; and
  elimination of nodes no longer associated with the pivot object.

5. The system of claim 1, wherein the instructions further cause the processor to configure the at least one communication channel based on previously collected channel configuration data retrieved from a channel configuration database.

6. The system of claim 1, wherein the instructions further cause the processor to record channel configuration data of the at least one communication channel into a channel configuration database.

7. The system of claim 1, wherein the instructions further cause the processor to identify pivot points corresponding to the pivot objects and store the pivot points in a channel configuration database, wherein the pivot objects are associated with data for communication among users of the nodes.

8. The system of claim 1, wherein the instructions further cause the processor to monitor a current workflow of an organization in real-time to generate a plurality of communication subchannels associated with pivot objects based on the current workflow.

9. The system of claim 1, wherein the instructions further cause the processor to provide indications to users of the nodes of the at least one organization network when at least one property of at least one pivot object associated with the nodes changes.

10. A method, comprising:
  monitoring at least one organization network to collect analytics data by a channel server node;
  processing, by the channel server node, the analytics data to identify nodes and associated pivot objects of the at least one organization network;
  querying, by the channel server node, workflow-related communication records of the at least one organization network to extract workflow communication data; and
  generating at least one communication channel configured to connect the nodes and the associated pivot objects based on the workflow communication data.

11. The method of claim 10, further comprising monitoring the pivot objects to detect changes in pivot object properties.

12. The method of claim 11, further comprising, responsive to a detection of changes in the pivot object properties, reconfiguring the at least one communication channel associated with the pivot object.

13. The method of claim 10, further comprising configuring the at least one communication channel based on previously collected channel configuration data retrieved from a channel configuration database.

14. The method of claim 10, further comprising recording channel configuration data of the at least one communication channel into a channel configuration database.

15. The method of claim 10, further comprising identifying pivot points corresponding to the pivot objects and storing the pivot points in a channel configuration database, wherein the pivot objects are associated with data for communication among users of the nodes.

16. The method of claim 10, further comprising monitoring a current workflow of an organization in real-time to generate a plurality of communication subchannels associated with pivot objects based on the current workflow.

17. The method of claim 10, further comprising providing indications to users of the nodes of the at least one organization network when at least one property of at least one pivot object associated with the nodes changes.

18. A non-transitory computer readable medium comprising instructions, that when read by a processor, cause the processor to perform:
  monitoring at least one organization network to collect analytics data;
  processing the analytics data to identify nodes and associated pivot objects of the at least one organization network;
  querying workflow-related communication records of the at least one organization network to extract workflow communication data; and
  generating at least one communication channel configured to connect the nodes and the associated pivot objects based on the workflow communication data.

19. The non-transitory computer readable medium of claim 18, further comprising instructions, that when read by the processor, cause the processor to monitor the pivot objects to detect changes in pivot object properties and, responsive to a detection of the changes in the pivot object properties, reconfigure the at least one communication channel associated with the pivot object.

20. The non-transitory computer readable medium of claim 18, further comprising instructions, that when read by the processor, cause the processor to identify pivot points corresponding to the pivot objects and store the pivot points in a channel configuration database, wherein the pivot objects are associated with data for communication among users of the nodes.

\* \* \* \* \*